US012249188B2

(12) United States Patent
Lodha et al.

(10) Patent No.: US 12,249,188 B2
(45) Date of Patent: Mar. 11, 2025

(54) ABSENTEE BALLOT SYSTEM AND METHOD USING CODES FOR MINIMIZING PANDEMIC EXPOSURE

(71) Applicant: Lalit Lodha, Boston, MA (US)

(72) Inventors: Lalit Lodha, Boston, MA (US); Joshua Huntington, Chandler, AZ (US)

( * ) Notice: Subject to any disclaimer, the term of this patent is extended or adjusted under 35 U.S.C. 154(b) by 532 days.

(21) Appl. No.: 17/582,942

(22) Filed: Jan. 24, 2022

(65) Prior Publication Data

US 2022/0198865 A1 Jun. 23, 2022

Related U.S. Application Data

(63) Continuation-in-part of application No. 16/870,979, filed on May 10, 2020, now Pat. No. 11,232,663.
(Continued)

(51) Int. Cl.
*G07C 13/00* (2006.01)
*G06Q 50/26* (2024.01)
(Continued)

(52) U.S. Cl.
CPC ............. *G07C 13/00* (2013.01); *G06Q 50/26* (2013.01); *G06Q 2230/00* (2013.01)

(58) Field of Classification Search
CPC ..................................................... G07C 13/00
See application file for complete search history.

(56) References Cited

U.S. PATENT DOCUMENTS

| 2013/0251214 A1* | 9/2013 | Chung | G06V 40/19 |
| | | | 382/116 |
| 2014/0207537 A1* | 7/2014 | Joyce | G07C 13/00 |
| | | | 705/12 |

(Continued)

*Primary Examiner* — Joseph H Feild
*Assistant Examiner* — Pameshanand Mahase
(74) *Attorney, Agent, or Firm* — Handal & Morofsky LLC; Anthony H. Handal

(57) ABSTRACT

The inventive apparatus for printing, sending, receiving and counting absentee ballots, comprises a printer for creating a plurality of ballots, each of the ballots bearing a unique code device containing a unique identification code and a would-be voter personal computing device for sending a communication from a would be voter requesting a ballot and for sending personal identification information. The personal computing device must receive a biometric to become activated. A board of elections computing device receives a communication from a would-be voter requesting a ballot, the board of elections computing device being operated by software which causes it to execute a number of program steps comprising verifying that the personal computing device must receive a biometric to become activated, receiving personal identification information from the would-be voter personal computing device, and comparing the received personal identification information with voter record information contained in the database of registered voter information a board of elections to determine whether the would-be voter is registered to vote. A balloted voter database is adapted for storing a notation of a positive identification of the would-be voter as a registered voter, and for storing in the balloted voter database a notation that the would be voter is to be sent one of the ballots. A scanning device is adapted for scanning the unique code device on one of the ballots. A sent ballots database stores the identification of the one ballot in the sent ballots database. A voted ballots database receives an indication that a communication has been received from the registered voter personal computing device of the would be voter, the communication comprising the output of a scan of the unique code device on the ballot sent to the would-be voter, the information including the unique identification code, whereby returned voted ballots may be assessed for authenticity, wherein the program of steps comprises assessing authenticity of return ballots by determining that each ballot is included in the sent ballots database and is included in the voted ballots database, (Continued)

whereby the ballots that are included in the sent ballots database and in the voted ballots database are identified as verified ballots, and the election choices in the verified ballots may be counted.

7 Claims, 34 Drawing Sheets

Related U.S. Application Data

(60) Provisional application No. 62/846,449, filed on May 10, 2019.

(51) Int. Cl.
*G07C 9/27* (2020.01)
*G16H 10/60* (2018.01)
*G16H 50/80* (2018.01)

(56) References Cited

U.S. PATENT DOCUMENTS

| | | | |
|---|---|---|---|
| 2014/0244512 A1* | 8/2014 | Liesenfelt | G06F 21/32 |
| | | | 705/51 |
| 2020/0258338 A1* | 8/2020 | Goswami | H04W 12/108 |
| 2021/0051017 A1* | 2/2021 | Durham, III | G07C 13/00 |
| 2021/0319642 A1* | 10/2021 | Boyd | G07C 13/00 |

* cited by examiner

Figure 1. Example of Mosaic
A Mosaic can vary in size
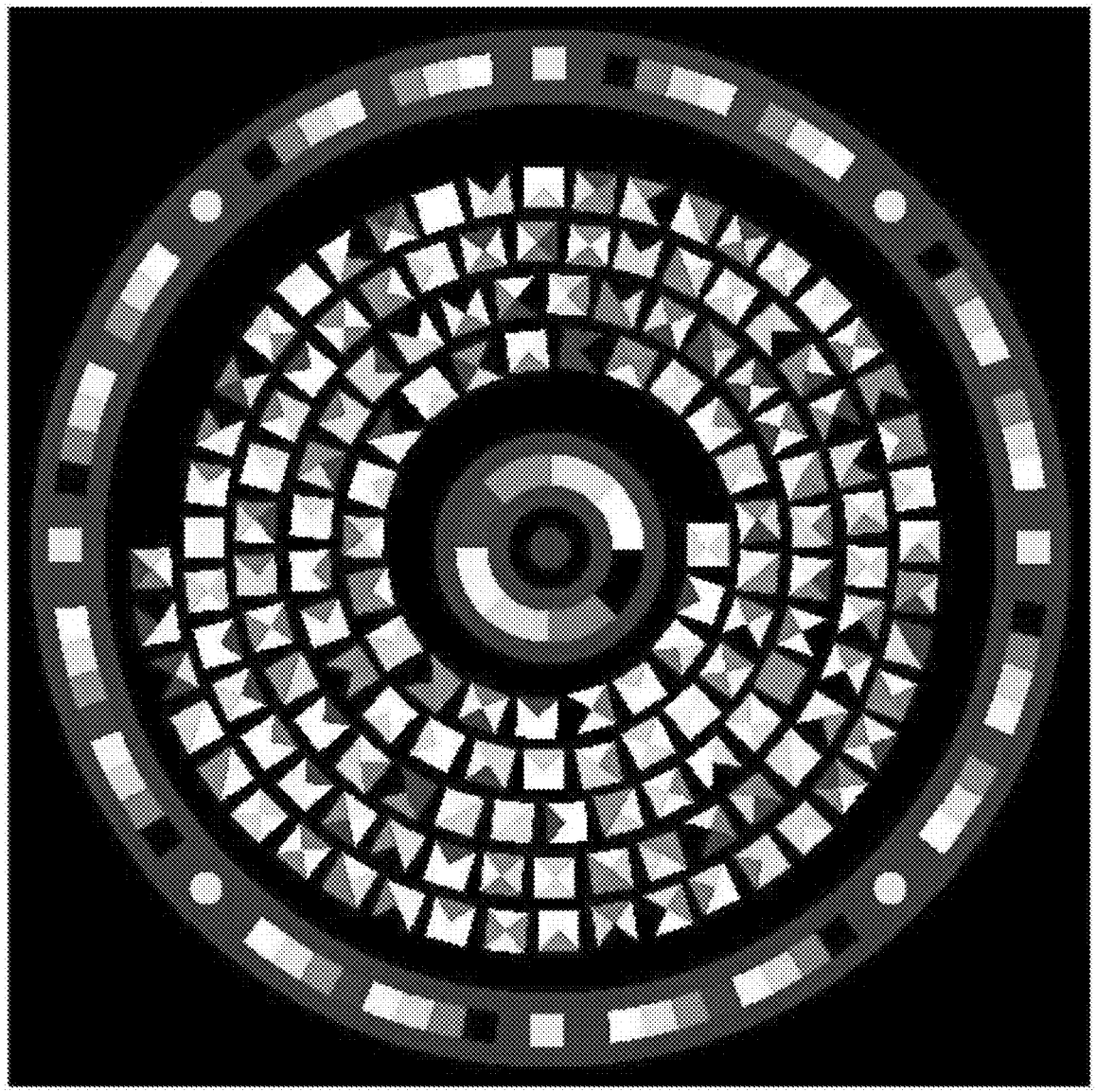

Figure 2. Another example of Mosaic
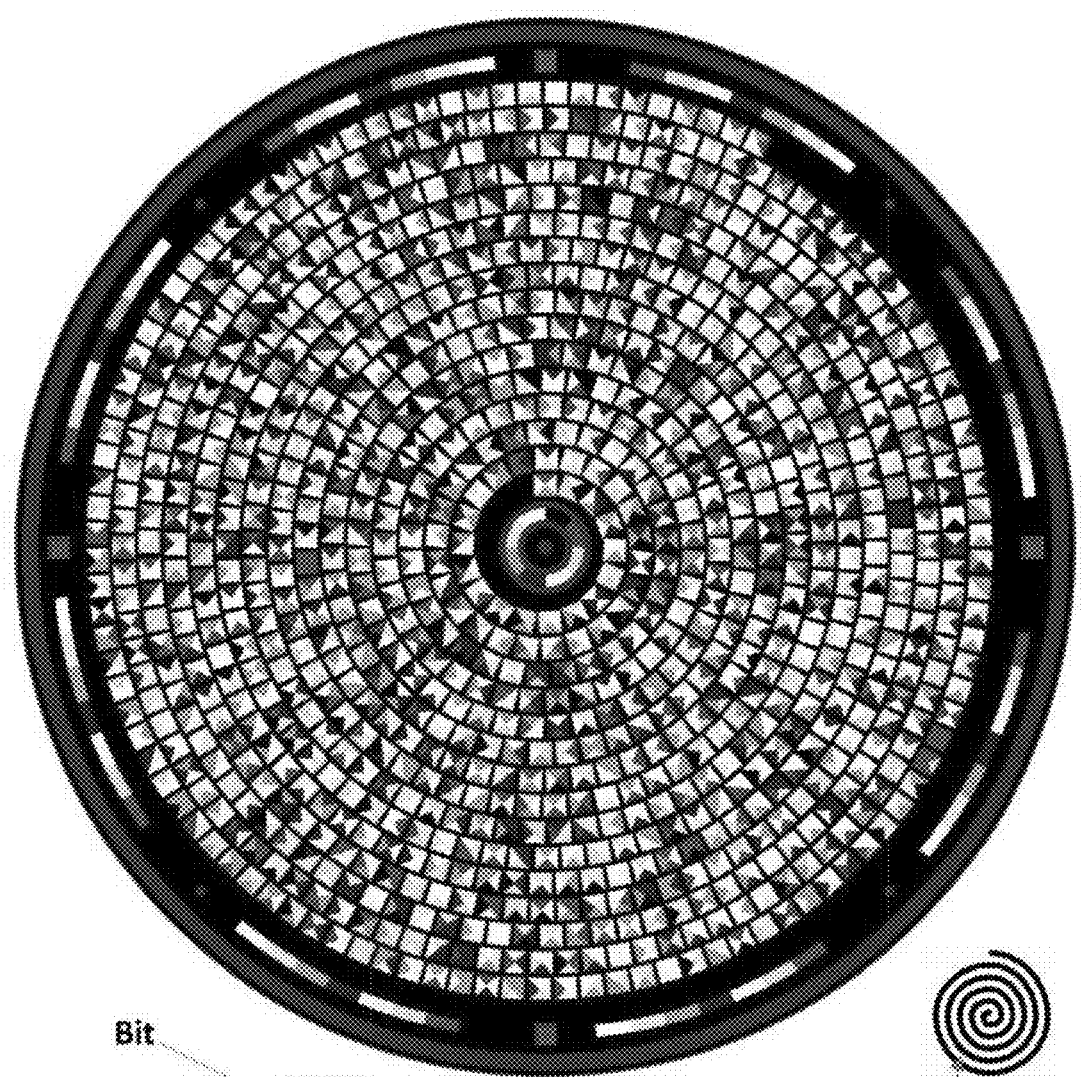
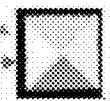
Bit
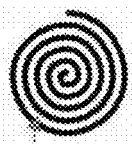
Fig 2.a. Mosaic is comprised of Bits (square as shown but can be any symbol, shape, picture or animation).
Fig 2.c. Bits are winding outward in a circular pattern. These Bits may go outward to the and turn around to come back in, then return out again till the pattern is complete.

Fig. 3 CLAIM #1 and 9 include but not limited to the following:
SHAPES OF MOSAIC – EXAMPLE
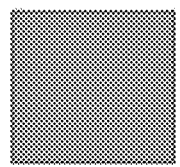 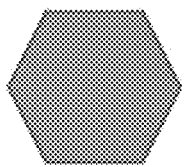 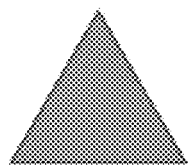 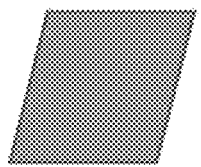
4 SIDED  HEXAGON  3 SIDED  4 SIDED PARALLELAGRAM
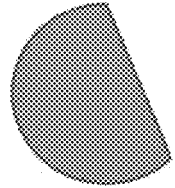
PART CIRCULAR SHAPE

Fig. 4: CLAIM #3 FLOW OF BITS – Which Bits to select & in what Sequence? (As illustrated below does not limit any flow not presented)
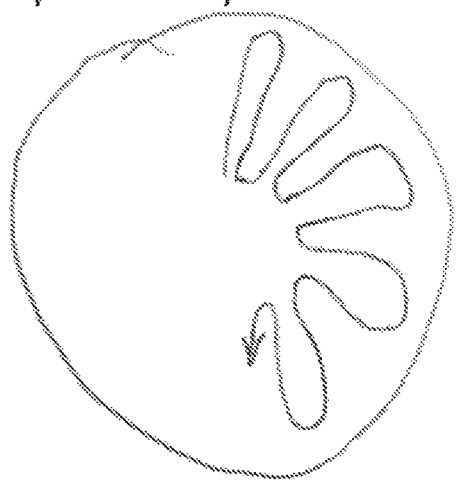
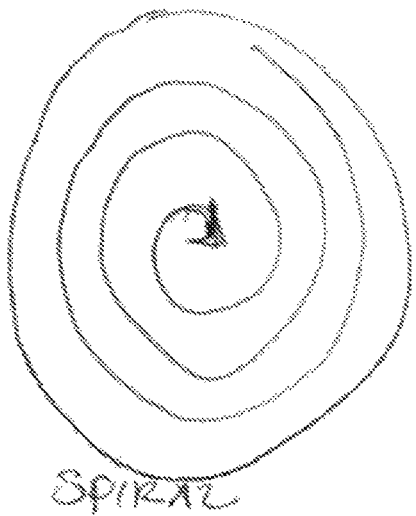
Fig 5 - In and Out
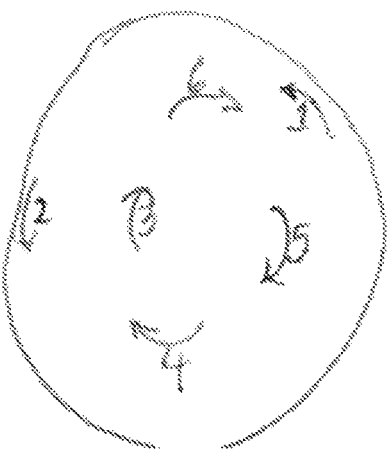
VARIOUS PATHS
PATH BASED ON PRE-DETERMINED EQUATIONS

Figure 6: CLAIM #5 The Bits will be extracted into a sequential message, the encoding of the message maybe in the order it was put together; or it may be in a determined order such as using every other bit.
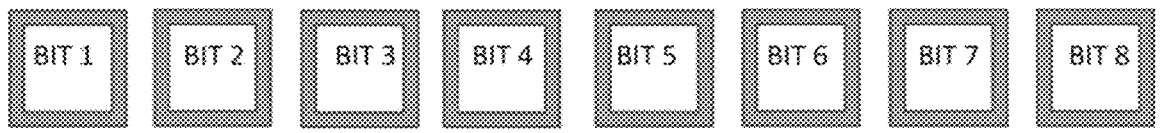
For example, a Fibonacci sequence will select bits 1,2,4,7

Figure 7. Another example of Mosaic
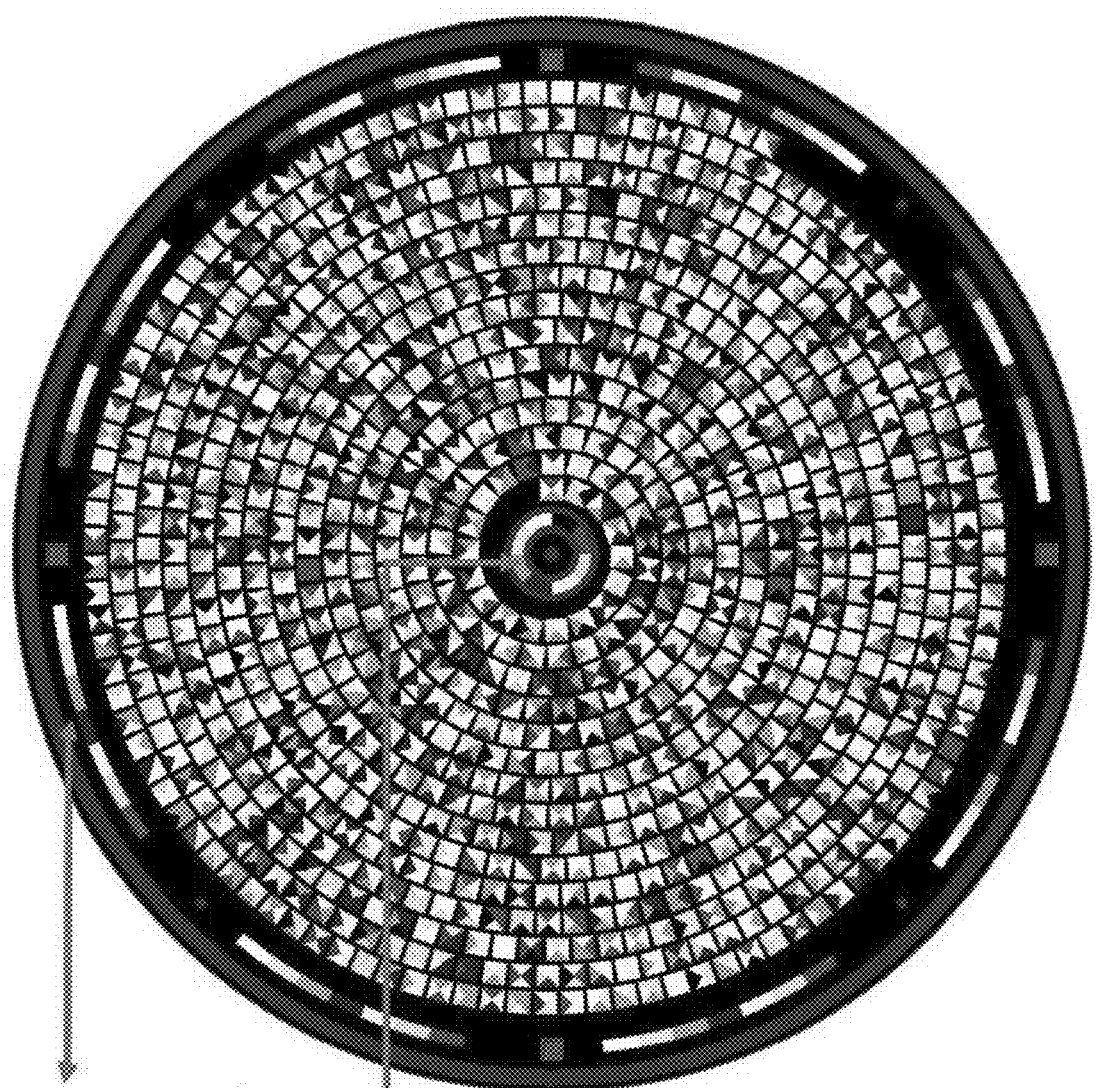
7. A color pallet is shown in the center of the Mosaic and a series of color pallets are shown at the edge of the Mosaic Figure 8: CLAIM #9 EXAMPLE OF BIT TYPES: ANY SHAPE, SYMBOL, PICTURE, ANIMATION

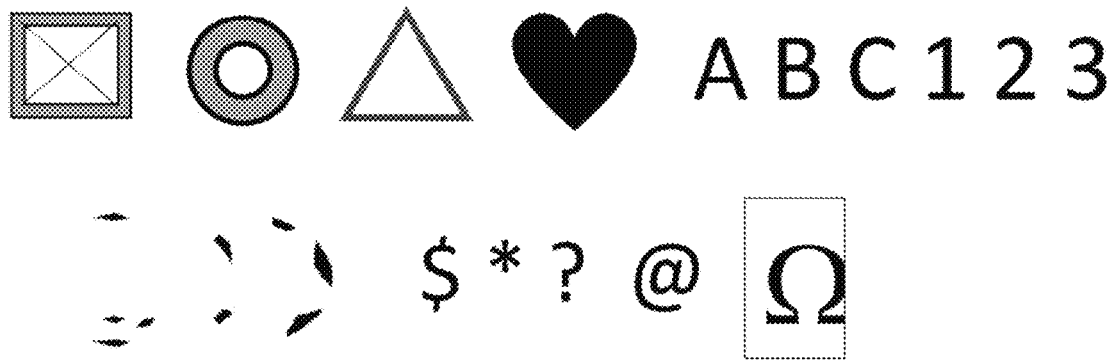

Figure 9: CLAIM #11: Each bit is optically encoded. Examples below show how these Bits can be optically different from each other. Please note that they may be colored in addition to be divided in the examples below

EXAMPLE OF BIT ENCODING BUT NOT LIMITED TO THE BELOW SET:

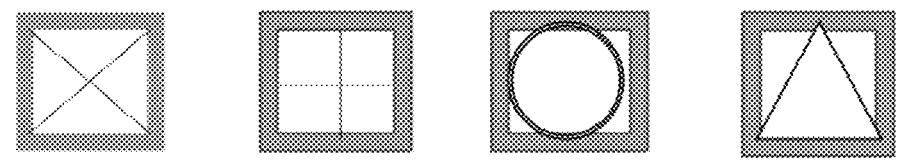

Fig. 10

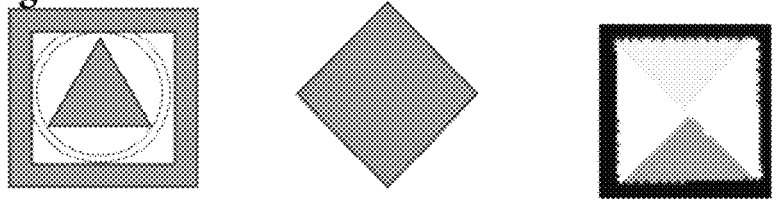

Any color may be used and instead of triangles, other shapes may be used to generate a Bit. A uni-color outline of a bit and the geometry that forms the bit may be used Figure 11: CLAIM 15
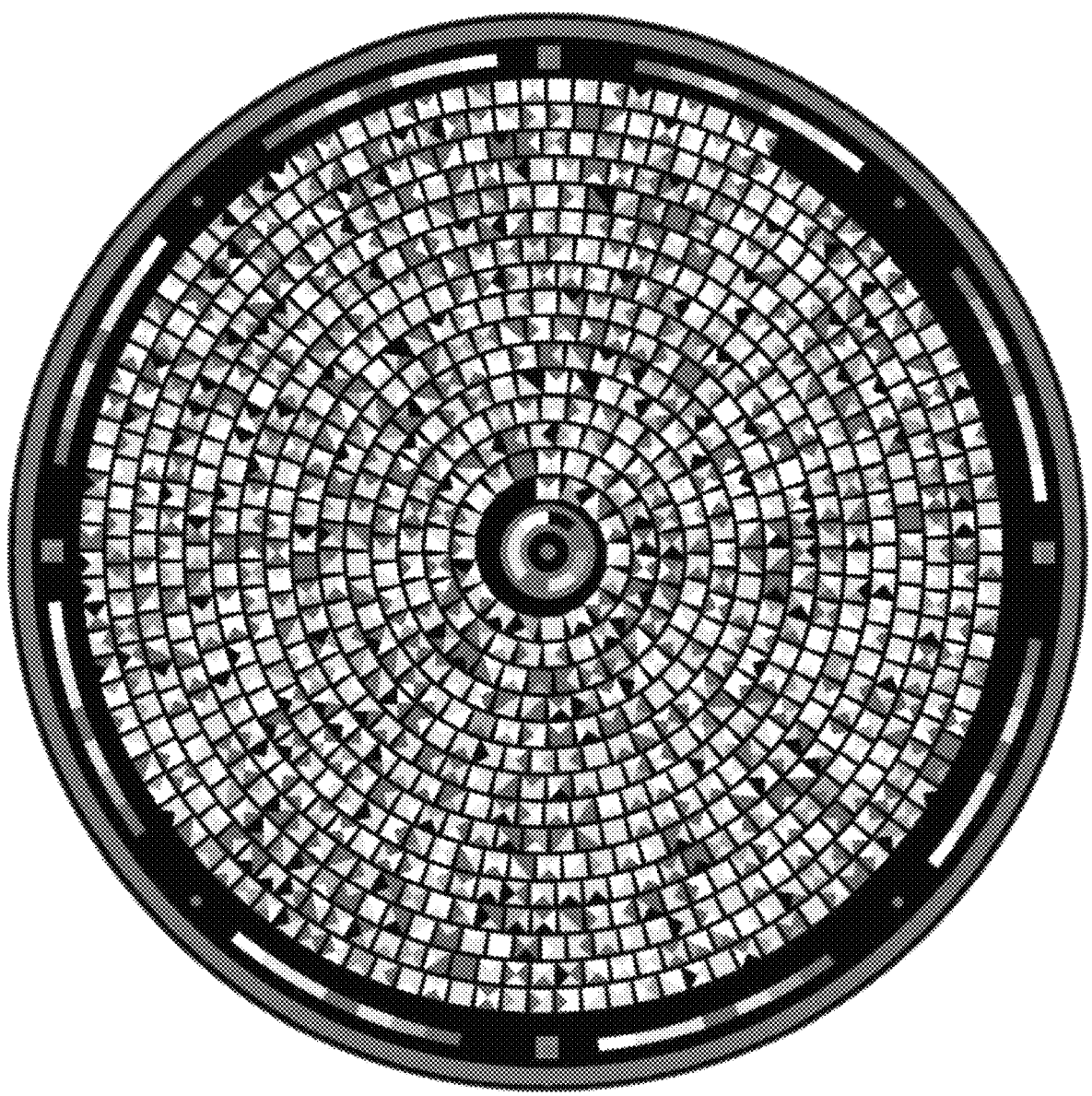

Figure 12: Usage examples
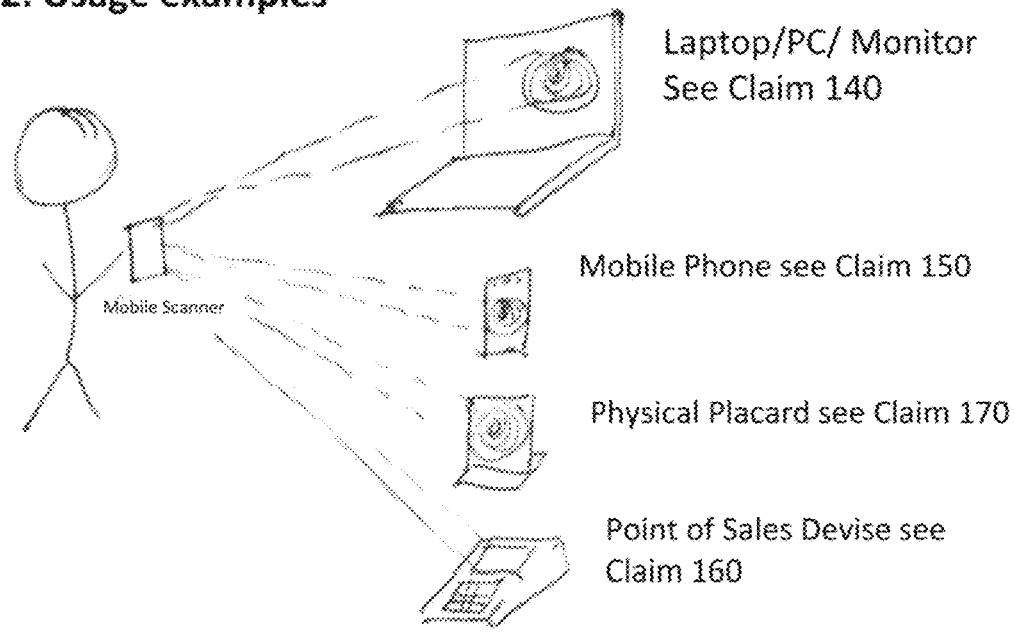
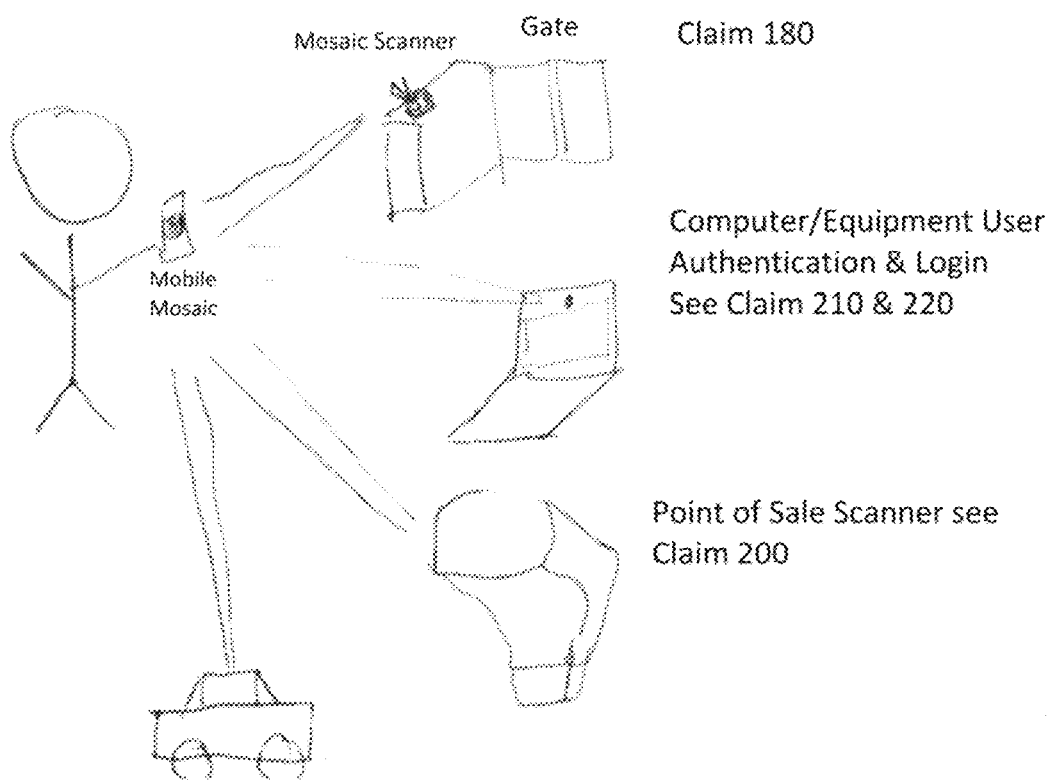

TIP: MOVE SCANNER TO FIT TARGET WITHIN GUIDES. NO BUTTONS NEED TO BE PRESSED. THE SCANNER WILL AUTOMATICALLY TAKE THE PICTURE AND THE GUIDES WILL FLASH WHEN THE TARGET IS RECOGNIZED.

STATUS: Identifying Target... (flashing) /Target Accepted

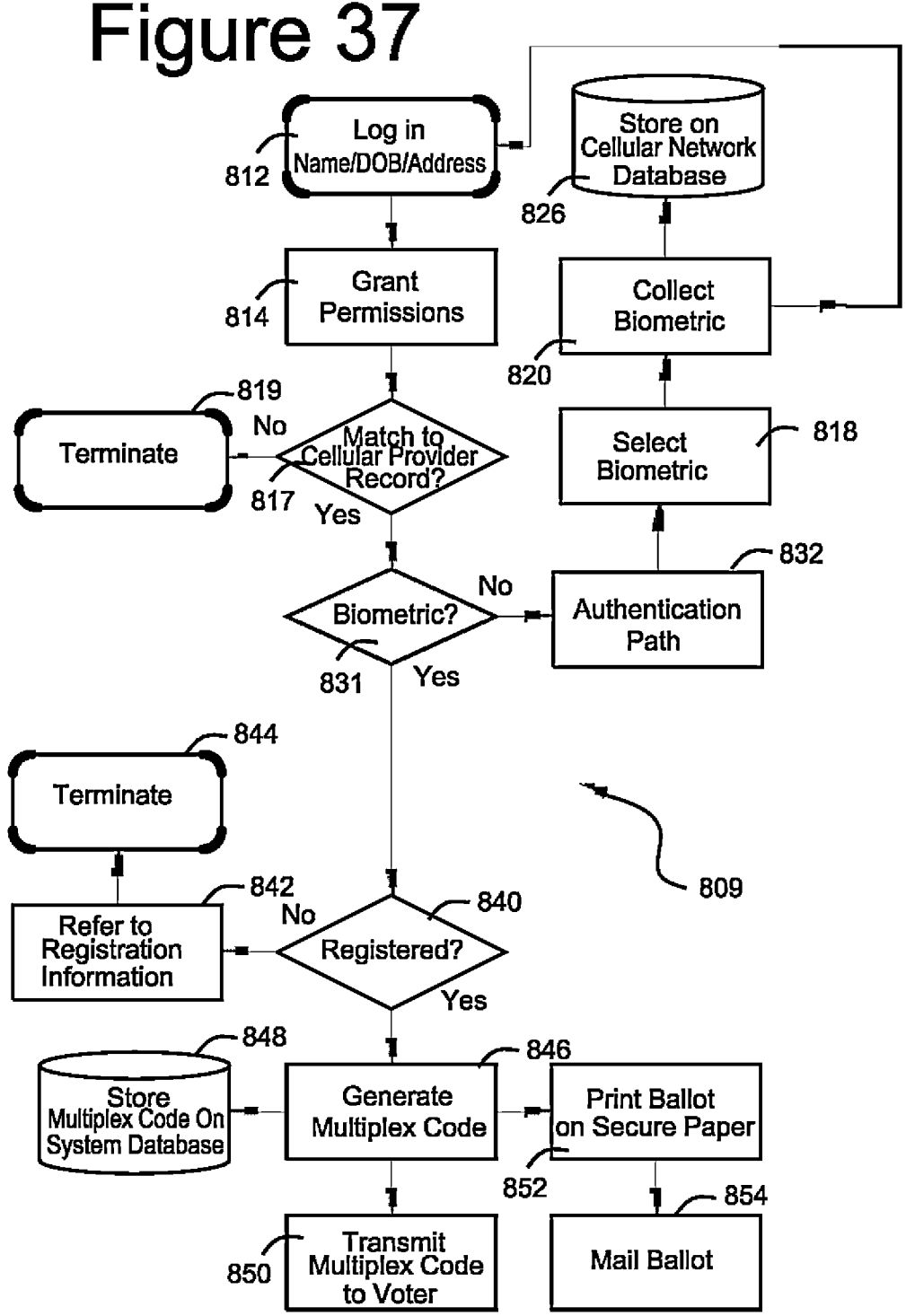

ABSENTEE BALLOT SYSTEM AND METHOD USING CODES FOR MINIMIZING PANDEMIC EXPOSURE

CROSS REFERENCE TO RELATED APPLICATIONS

This application is a continuation in part of and claims the benefit of the priority of U.S. patent application Ser. No. 16/870,979 filed by the inventors herein on May 10, 2020 and entitled System and Method Using Optical Tags to Conduct Secure Transactions and Authentications, now assigned U.S. Pat. No. 11,232,663 and expected to issue on Jan. 25, 2022. This application also claims the benefit of the priority of Provisional Patent Application No. 62/846,449, filed May 10, 2019, and entitled A System of Using Optical Tags to Conduct Secure Transactions and Authentications. The disclosures of the above applications and the information contained in their file histories are hereby incorporated herein by reference.

TECHNICAL FIELD

The invention relates to apparatus and methods for safely from a health standpoint and securely creating, filling out and counting absentee ballots using an app for a mobile device such as a mobile phone or tablet in order to minimize exposure of voters and board of election staff to highly communicable infectious diseases such as Covid-19.

STATEMENT REGARDING FEDERALLY SPONSORED RESEARCH OR DEVELOPMENT (Not applicable)

BACKGROUND OF THE INVENTION

Today, the manner in which a bricks and mortar transaction is conducted is via cash, credit/debit/gfft/store cards, and, if a merchant accepts the same, PayPal from a Point of Sale (POS) device. New technology such as that offered by Apple called ApplePay includes a wireless method of conducting a transaction using NFC (Near Field Communication) chips, POS and wireless protocol. This requires the vendor to use a POS that is equipped with NFC technology. Finally, there are new cloud-based payment schemes such as Venmo, which work by supplying credit/debit card or bank account information, and can facilitate transfer of money without the need to make a physical transaction at a POS device. This technology can facilitate person-to-person transactions, as well as e-commerce transactions.

Online transactions require input of credit/bank/gift/store card information at the point of sale on the website. Certain websites allow the use of Paypal and Amazon services. These services keep all of the credit card information internally for easy use, for example in the case of subsequent purchases.

However, with some of these methods, the use of cards can be a security concern. With methods like Paypal, the need to enter a password is a security concern. With other methods, such as with Venmo, there is no way to locally authenticate the buying and selling parties, which makes POS use, both for e-commerce and brick and mortar difficult and insecure.

In China, almost all consumer transactions use a QR code offered by Alibaba using their service called AliPay. QR codes are insecure but because they are ubiquitous, they have become the de facto standard throughout China. Applications include such a wide diversity of things as admission to a tourist attraction and buying fruit from a local street merchant. Accordingly, QR codes are ubiquitous throughout China. While it has not yet become a serious issue, there are many payment scenarios where it is vital to authenticate the buyer and the seller, and security issues are a potential serious concern in the future.

Given that our world is moving in the direction of ever increasing online activity, identity theft, already very prevalent and causing billions of dollars in damage, aggravation and time spent in undoing the damage, is an increasingly serious concern. A system to by-pass transmitting personal information yet offer the flexibility of conducting important and needed transactions such as self-authentication and purchasing is thus needed to match the increasingly important online paradigm.

At the same time, other threats make the implementation of secure and reliable identification of parties and their actions increasingly important.

SUMMARY OF THE INVENTION

The invention relates to apparatus and methods for securely authenticating information such as the identity of an individual (for example a consumer-user of the inventive system and apparatus), an attribute of the individual, an attribute of information associated with an individual (such as a bank account balance, a medical condition, vulnerability or advantage or a psychological condition), or other attribute of. Such authentication is implemented in the system which may be used for conducting brick and mortar commerce, e-commerce, maintaining a safe environment or the like.

The same is achieved with reference to a secure record. Such use may be in the context of authentications using a mobile device such as a mobile phone or tablet. In addition, the authentication procedure may be used to augment information or change information on a record associated with the individual. The same is facilitated by a multiplex code ("multiplex" or "multiplex code"), which is similar to a barcode or QR code but includes higher density capabilities optionally enabled by nonlinear sub element layouts, multiple colors and multi-shaped multielement sub element components as more fully appears herein.

More specifically, in accordance with the invention, the inventive apparatus may use the camera feature of a consumer user's mobile device or optionally RFID tag recognition device capabilities to securely initiate a transaction with a thereafter authenticated business entity, for example a commercial establishment displaying the inventive multiplex code at the entrance to that commercial establishment. Similarly, the commercial establishment may authenticate the consumer user by reading a multiplex code or other code displayed on the, for example, smart device of the consumer user.

More particularly, it is contemplated that, for example, the consumer user may use a smart device, such as a smart phone, to scan a sticker with a multiplex code adhered to the door of a commercial establishment, causing the smart phone to read commercial establishment identification information and transmit the same to the server of the operator of the inventive system, for example, one accessible as an operator's website over the Internet. The server then transmits an authentication code to the smart device of the consumer user, and that authentication code is displayed by the smart device as a confirmation of the authentication sought. An automatic device or an individual with another smart phone, for example, or other device may then scan the authentication code on the smart phone of the consumer user, to complete the authentication procedure, and thus allow the object of the authentication, such as the charging of an account, admission to a facility, and so forth.

A particular application involves the certification of an individual as having antibodies for an infectious condition, and thus perceived as a low risk for transmission of that infectious condition. More particularly, the object of this particular application is the creation of a safe space where cleared individuals may congregate substantially without a risk of infection or infecting others. Such application is of particular use to, for example, restaurant operators whose employees would wish to avoid exposure to large numbers of individuals potentially spreading an infectious pathogen, such as SARS-CoV-2, responsible for the coronavirus pandemic of 2020. First, in this application, an authentication procedure begins with the individual accessing, for example, the website of the operator of the inventive system and inputting alphanumeric identification information as well as a biometric input, such as a face, fingerprint or other authenticating input. That information is then, together with the alphanumeric information, sent to the operator of the inventive system completing an enrollment process for the consumer user, and resulting in populating the system database with identification information including the biometric input and the alphanumeric information input by the consumer user.

Next, the enrolled consumer user then goes to a medical professional who performs a medical test for the existence of the protective antibodies and the same information is securely certified to and authenticated in the system database. In this particular example, the population of the system database with such medical information completes the medical condition certification process.

Thirdly, once the consumer user is enrolled in the first step of the process and authenticated with the particular, for example, medical attribute, the system uses an authentication process using the multiplex code to allow the consumer user access to the safe space.

In accordance with another embodiment of the invention, a method and system is disclosed which relates to online information transfer via interface surfaces printed or displayed with information and coded data. The coded data may be scanned with an appropriate scanning device. The scanning device communicates with a computer system to authorize the release of information. Together, the interface surfaces, sensing device and computer system are capable of effecting transactions over a network.

The inventive system for the secure transfer of information, enables a user to use a mobile device to securely transfer information using a generated optical machine readable image. In an embodiment, the user scans the encoded, scannable mobile device image that is displayed by the party requesting information (merchant, doctor, other entity) to initiate a transaction. The system completes the transaction by processing information between decryption software residing on either the user's mobile device and/or the computer system, which will authorize release of information through a transaction server or on an application residing on a requestor's device.

The method using a computer-generated code design, referred to herein as a multiplex code, that comprises a plurality of digital tiles or images to authorize payment. A plurality of digital tiles are arranged in a pattern to form a multiplex code-like design, formed as a plurality of "tiles" and functioning as an optically scannable tag. The specific contents of the digital tiles can be decoded using known methods (e.g. static or dynamic codebooks).

The present invention uses a novel identifier called an optically scannable tag that stores an encrypted/hashed message within the optically scannable tag image which is comprised of a unique pattern of digital tiles (formed by elements consisting of one or more pixels), and laid out in a tilework-like pattern. Because it is encrypted/hashed, the message can be considered secure and used to uniquely identify the transaction between parties within an authentication scheme.

The optically scannable tag methodology is also a uniquely secure way of authenticating the optically scannable tag holder and the optically scannable tag scanner. Each party generates a unique and secure time sensitive encrypted/hashed token that is used to authenticate each party. If the tag is dynamically generated, it is, once validated, an authentication of the owner of the tag. The transaction is also authenticated using the optical tag. A camera (e.g. mobile phone camera) scans the tag image and translates it and decrypts it either on the device or on the cloud. This information identifies the transaction (e.g. purchase, validation of users) and is used for further security action in the cloud. The scanning action initiates the transaction.

In principle, the inventive system may utilize a dynamic book. More particularly, an optically scannable tag is requested by one party, for example, the seller. The optically scannable tag is generated (typically in the cloud) and sent to the seller and displayed. The purchaser scans the optically scannable tag using a downloaded application which is associated with the operator of the inventive system. This scan first reads the multiplex code and produces a rasterized image of the same. Using a specified methodology, the rasterized image is translated into a series of digital tiles (e.g., squares)—this may be combined with the next step. Using another specified methodology, the digital tiles are thereafter decoded from their optical view (the colored digital tiles) and stitched into an encrypted/hashed message that can be decrypted and used for the pending transaction or pending authorization.

Alternatively, a static book approach maybe used. For example, a tag may be created in advance and used by the tag owning party to direct a transaction with partial authentication of the tag owning party. The scanning party scans the tag and is given information about the owner, which the scanning party then, optionally, validates in real time outside of the scope of the program (e.g. validate name and address of owner visually).

The dynamic scanning process is novel because it validates each party with their own unique digital mark (e.g. biometric such as a thumb print, face or other personal marker). It is also novel because the transaction itself is authenticated. It is also novel because it is streamlined and does not involve the unnecessary participation of the user. This means that no unnecessary button pressing or the like is needed, beyond pointing to the optically scannable tag and confirming/inputting the transaction. Thus, a purchasing transaction essentially only needs to actions.

Because the user does not enter a password on the electronic device (e.g. laptop) or provide any credit card information to the merchant at the time of purchase, the frailties of security loopholes, present in systems which use such information, are closed to anyone sniffing keystrokes or monitoring transactions on the network.

The scanning process is also novel because it uses optical scanning, optical decoding, message stitching and message decrypting as a means to create ease of use, flexibility of use and security in use.

The optically scannable tag is, compared with conventional QR code, more sophisticated and secure by virtue of its higher information density, as well as its nonlinear pattern and multicolor format. It is noted that security may be enhanced by varying the nonlinear pattern with each transaction, as well as varying the color palette of colors used, thus complicating the task of would be hackers. In preferred embodiments, a multi-colored tag is generated for each transaction where each tag comprises a unique pattern of digital tiles that can be securely sent over networks with decryption only happening on the local device.

Though very useful in financial transactions, this system may also be used as a conduit to transmit other critical data dynamically (e.g. medical data), particularly in the context of creating safe environments as detailed above.

Thus the inventive system is capable of application in the most challenging of environments where security is of paramount important for a transaction, or for other aspects of human interaction.

In accordance with the invention, a method is provided for authentication applicable, for example, to controlling access to a space. A plurality of sets of consumer user identification information associated with a plurality of consumer users are received and stored in a consumer user database. A plurality of biometric identifiers, each of the biometric identifiers being associated with an associated one of the plurality of consumer users are received and stored in the consumer user database with associative information associating each biometric identifier with its associated consumer user to form an enrollment record. Verification is made of the identity of a presented individual by receiving a presented set of consumer user identification information from the individual whose identity is to be verified, acquiring a locally generated biometric identifier of the type stored in the consumer user database directly from the individual whose identity is to be verified, comparing the presented set of consumer user identification information to the sets of consumer user identification information stored in the consumer user database to determine whether there is a match between consumer user identification information stored in the database and the presented set of consumer user identification information, and comparing the locally generated biometric identifier to biometric identifiers stored in the consumer user database to determine whether there is a match between biometric identifiers stored in the consumer user database and the locally generated biometric identifier.

A comparison verification signal is generated in response to the determination that the presented set of consumer user identification information and the locally generated biometric identifier match a set of consumer user identification information and its associated biometric identifier. A certification procedure is performed with respect to the presented individual to generate a certification result. The certification result is stored in the consumer user database. A particular communications device associated with a particular consumer user is provided, in response to a request originated from the particular portable communications device with an identification signal in a format which may be read by a device at a commercial or social establishment is a verification that the consumer user has been verified. The particular consumer user is then provided with access to the establishment.

The plurality of sets of consumer user identification information associated with a plurality of consumer users may be stored in memory associated with a server operated by a website operator, and wherein the storing is implemented by transmission to the server over the Internet.

The biometric identifiers are stored in memory associated with the server and the communications device of the user consumer may be a portable communications device.

The above verification steps may be performed by a certified service provider's accessing the server of the website operator over the Internet.

A certification procedure may be performed with respect to the presented individual to generate a certification result by performing a psychological interview.

The certification procedure may be performed by verifying a balance in a monetary account maintained by the consumer user, and such action may be followed by the charging of a monetary amount to the monetary account maintained by the consumer user.

The establishment may use a publicly displayed and publically accessible coded information device, and the request may be generated in response to reading of the coded information device by the particular portable communications device associated with the particular consumer user.

The coded information device may be a coded graphic which identifies the establishment, and wherein the particular portable communications device associated with the particular consumer user transmits identification information to the server of the website operator. The server operated by the website operator, in response to the reception of the transmitted identification information associated with the establishment and identification information associated with the particular consumer user, may transmit an admission signal to the establishment.

Optionally, the coded graphic may have a nonlinear layout and multiple colors. The layout may be varied from transaction to transaction. Likewise the pallet of available colors for the coded graphic may vary from transaction to transaction with the object of complicating any attempted breach of the security of the system.

The admission signal may operate a lock at the door of the establishment to allow entry to the establishment by the particular consumer user.

Optionally, the establishment may be an automobile for hire and the lock may be an automotive door lock.

The identification information may be transmitted to the server over the Internet, causing the server to transmit a code which is optically displayed on the particular communications device, and the code on the phone maybe scanned at the establishment and in order to unlock the door to the establishment.

The inventive method for printing, sending, receiving and counting absentee ballots, comprises creating a plurality of ballots, each of the ballots bearing a unique code device containing a unique identification code receiving a communication from a would-be voter requesting a ballot, the communication being initiated from a personal computing device. The personal computing device is verified as being of the type which must receive a biometric to become activated. A personal identification information from the would-be voter. The received personal identification information is compared with voter record information contained in the database of registered voter information to determine whether the would-be voter is registered to vote. In response to a positive identification of the would-be voter as a registered voter, the restored in a balloted voter database a notation that the would be voter is to be sent one of the ballots. A unique code device on one of the ballots is scanned and the identification of the ballot is stored in a sent ballots database. A ballot whose identification is noted in the sent ballots database is sent to the would-be voter. A communication is received from the registered voter using a personal computing device which can only be activated by a biometric, the communication comprising the output of a scan of the unique code device on the ballot sent to the would-be voter, the information including the unique identification code. In response to the communication from the registered voter comprising the output of the scan of the unique code device on the ballot, the unique identification code of the scaned ballot is stored in a voted ballots database. The scanned ballot is received from the would-be voter annotated with election choices. The above steps are repeated for a plurality of voters. For each of the ballots received from would-be voters, it is verified that each ballot is included in the sent ballots database and is included in the voted ballots database, whereby the ballots that are included in the sent ballots database and in the voted ballots database are identified as verified ballots. The election choices in the verified ballots are then counted.

The unique code device may comprise an optically readable code or a a near field communication device.

4. A method as in claim 2 wherein verifying that the personal computing device must receive a biometric to become activated; noting the identification of the computing device in a ballot computing device database.

The inventive apparatus for printing, sending, receiving and counting absentee ballots, comprises a printer for creating a plurality of ballots, each of the ballots bearing a unique code device containing a unique identification code and a would-be voter personal computing device for sending a communication from a would be voter requesting a ballot and for sending personal identification information. The personal computing device must receive a biometric to become activated. A board of elections computing device receives a communication from a would-be voter requesting a ballot, the board of elections computing device being operated by software which causes it to execute a number of program steps comprising verifying that the personal computing device must receive a biometric to become activated, receiving personal identification information from the would-be voter personal computing device, and comparing the received personal identification information with voter record information contained in the database of registered voter information a board of elections to determine whether the would-be voter is registered to vote. A balloted voter database is adapted for storing a notation of a positive identification of the would-be voter as a registered voter, and for storing in the balloted voter database a notation that the would be voter is to be sent one of the ballots. A scanning device is adapted for scanning the unique code device on one of the ballots. A sent ballots database stores the identification of the one ballot in the sent ballots database. A voted ballots database receives an indication that a communication has been received from the registered voter personal computing device of the would be voter, the communication comprising the output of a scan of the unique code device on the ballot sent to the would-be voter, the information including the unique identification code, whereby returned voted ballots may be assessed for authenticity, wherein the program of steps comprises assessing authenticity of return ballots by determining that each ballot is included in the sent ballots database and is included in the voted ballots database, whereby the ballots that are included in the sent ballots database and in the voted ballots database are identified as verified ballots, and the election choices in the verified ballots may be counted.

BRIEF DESCRIPTION OF THE DRAWINGS

The operation of the inventive system and its methodology will become apparent from the following description taken in conjunction with the drawings, in which:

FIG. 1 illustrates a multiplex code in accordance with the present invention;

FIG. 2 illustrates an alternative multiplex code;

FIG. 3 illustrates shapes which may be employed in the tiles of the inventive multiplex code;

FIG. 4 illustrates in and out and spiral patterns of tiles according to the present invention;

FIG. 5 illustrates various path and path based patterns of tiles according to the present invention;

FIG. 6 illustrates the extraction of bits;

FIG. 7 illustrates yet another pattern for a multiplex code in accordance with the invention;

FIG. 8 illustrates other types according to the present;

FIGS. 9 and 10 illustrate optical bit encoding in accordance with the invention;

FIG. 11 illustrates an alternative embodiment of multiplex code of the present invention;

FIG. 12 illustrates examples of usage of the inventive method;

FIG. 37 illustrates an alternative embodiment for the generation of a paper absentee ballot.

DETAILED DESCRIPTION OF THE PREFERRED EMBODIMENTS

Figure 13:
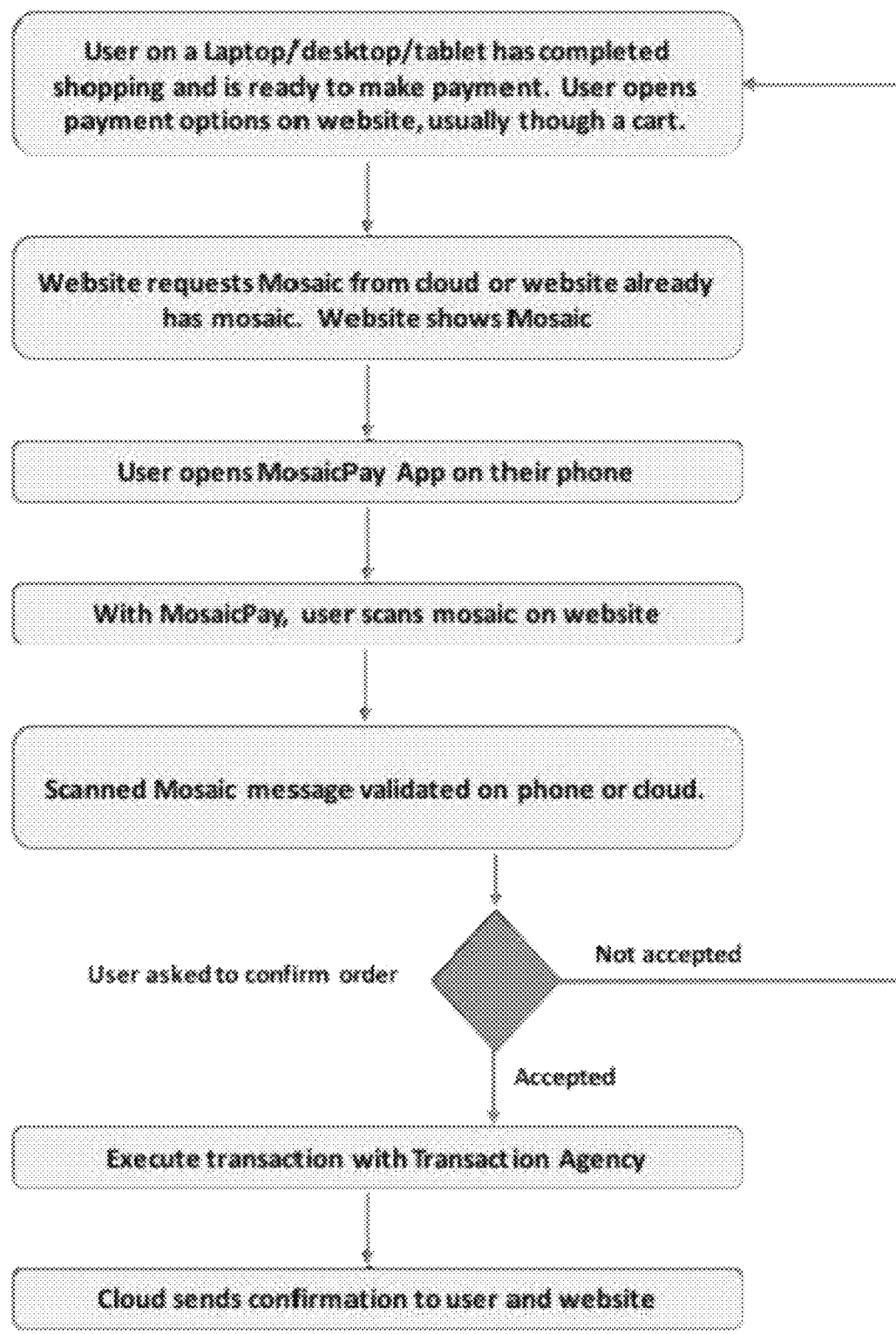
FIGS. 13-20 is a flow chart generally illustrating a general implementation of the present invention.
Figure 14:
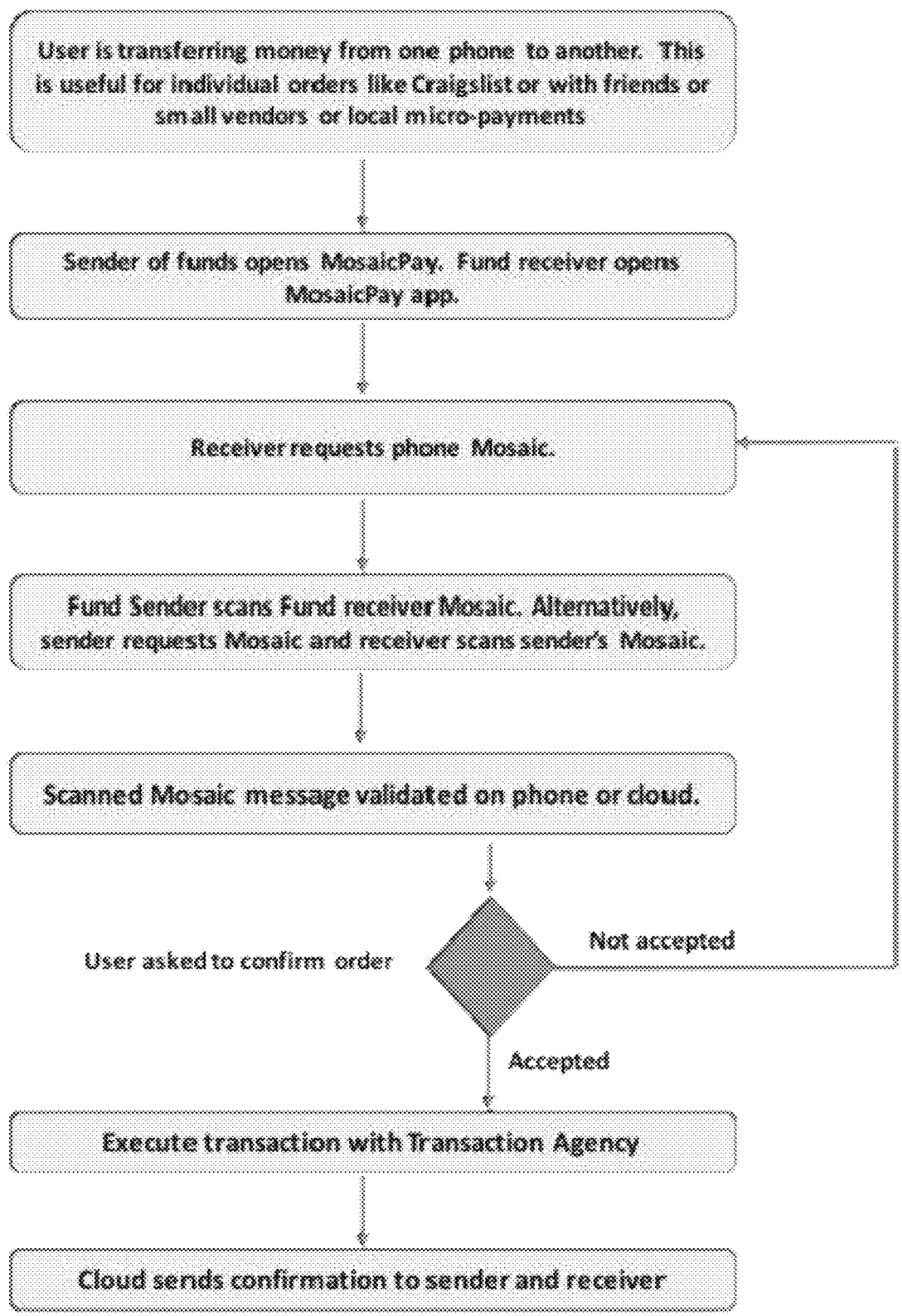
Figure 15:
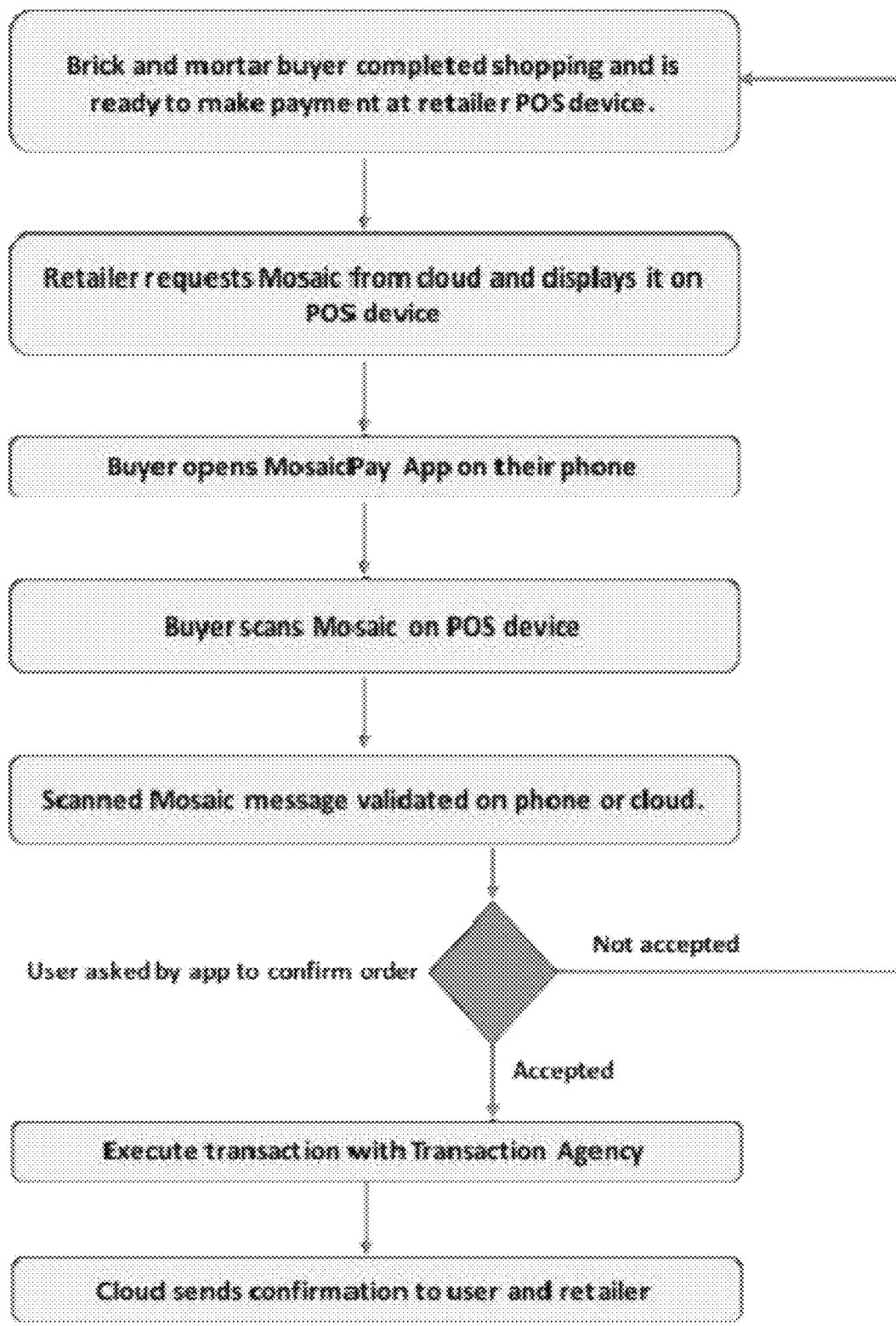
Figure 16:
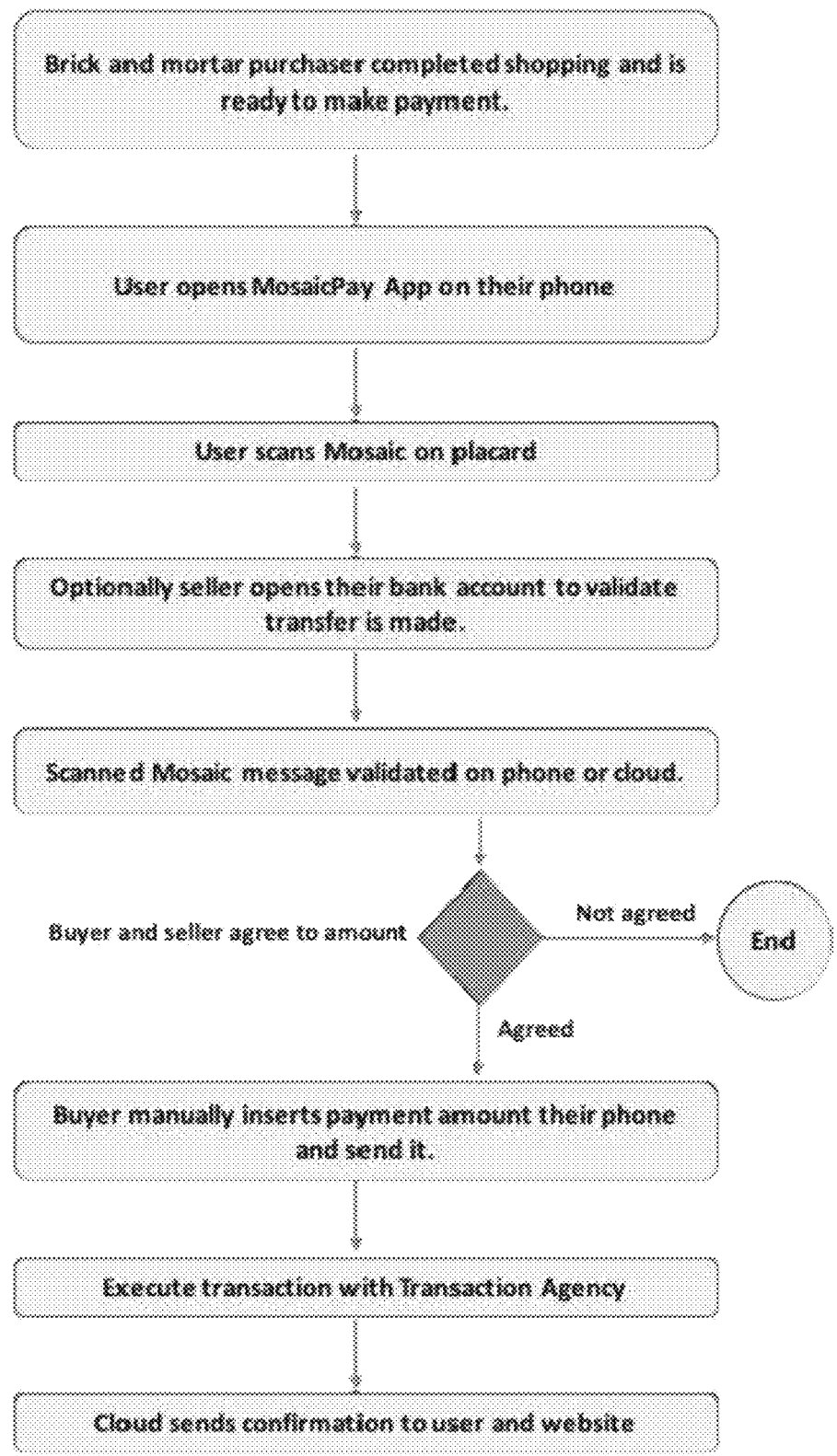
Figure 17:
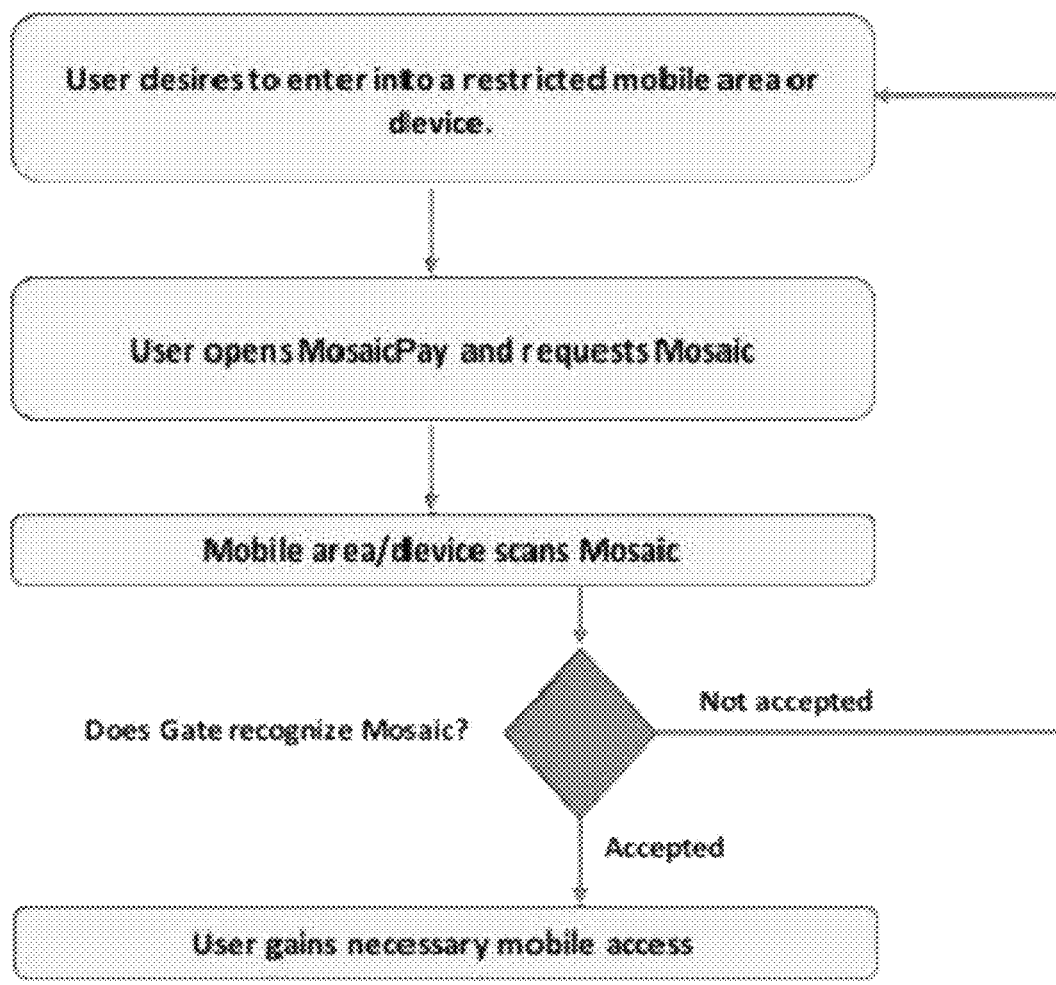
Figure 18:
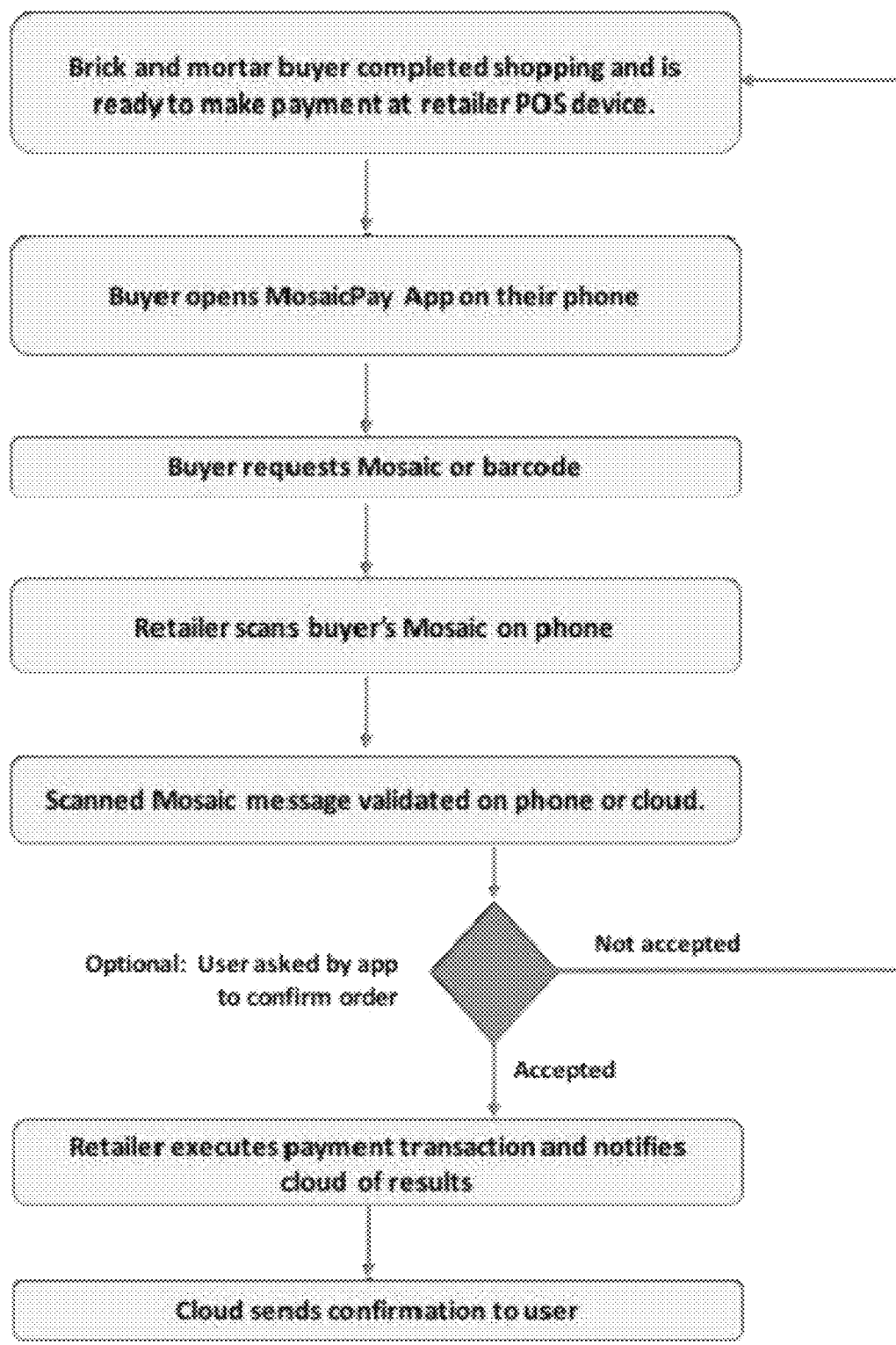
Figure 19:
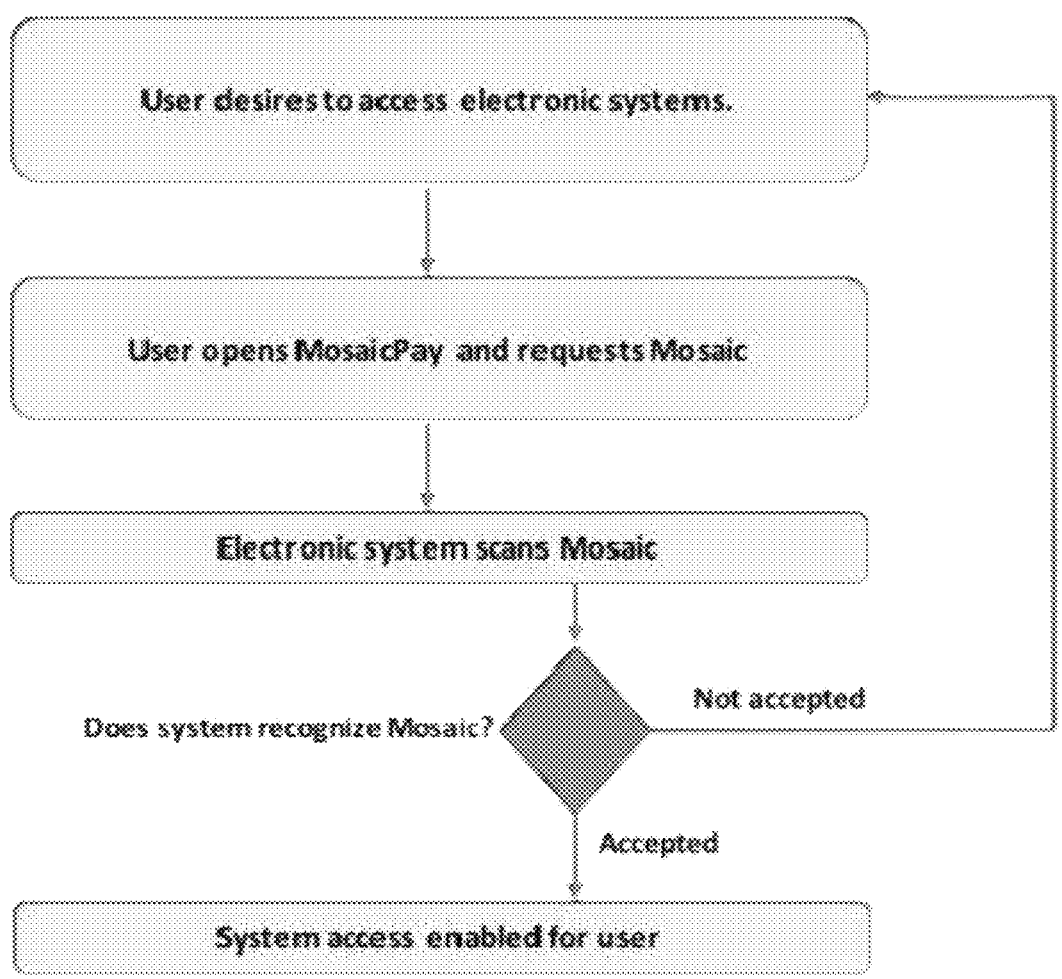
Figure 20:
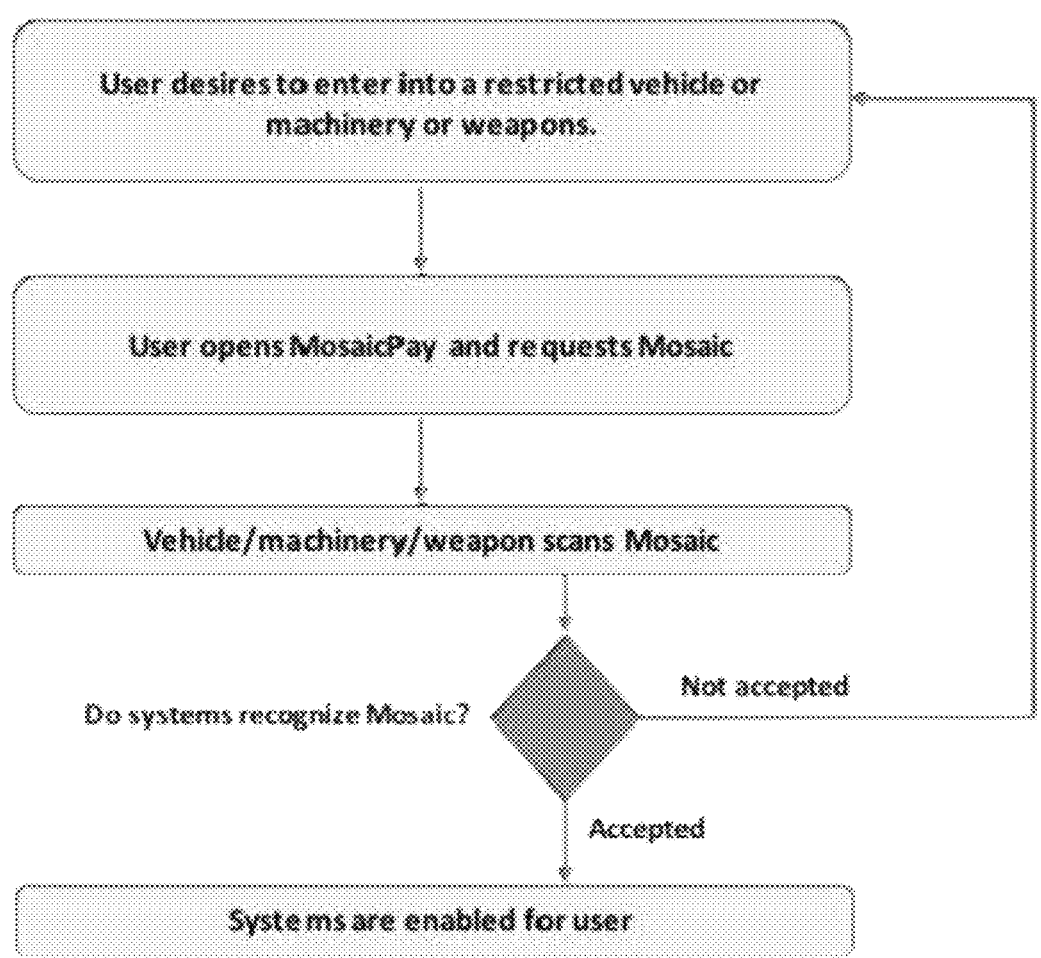
Figure 21:
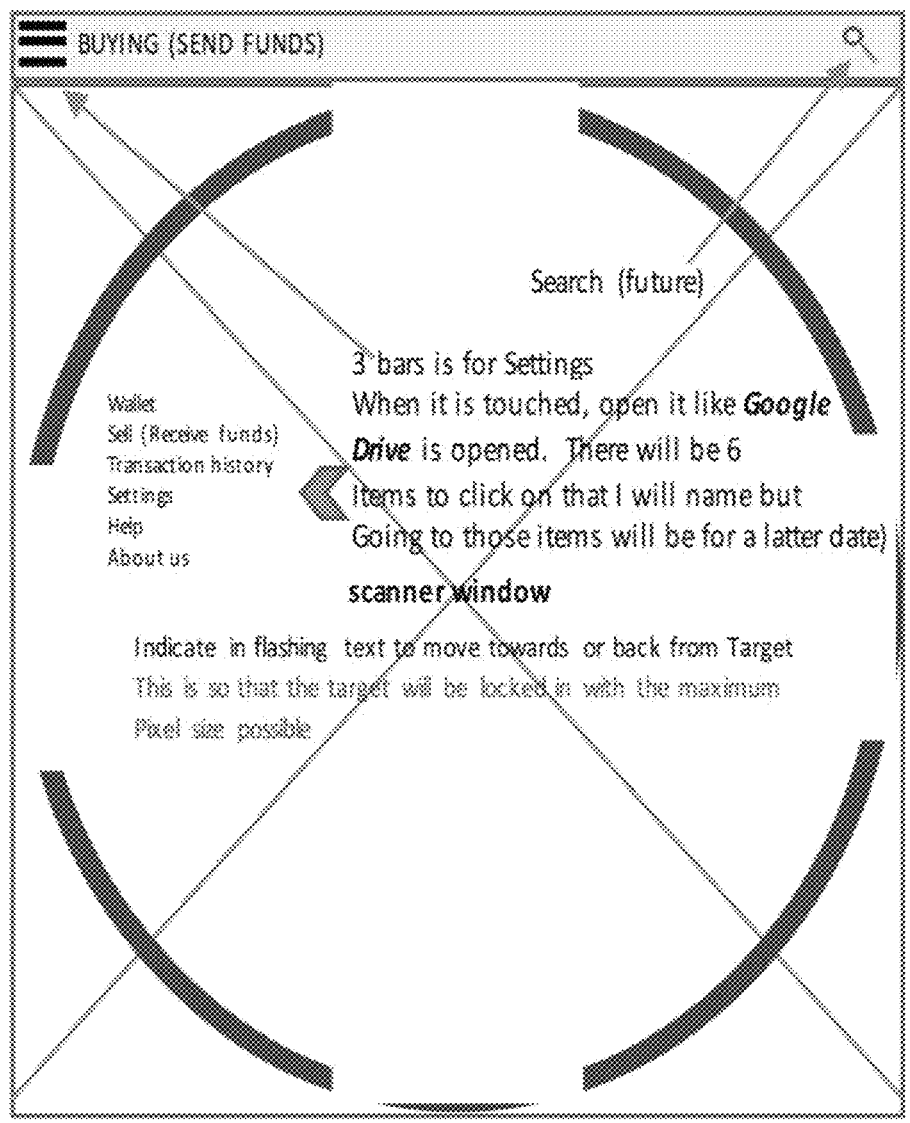
FIG. 21 illustrates an app screen according to the present invention.
Figure 22:
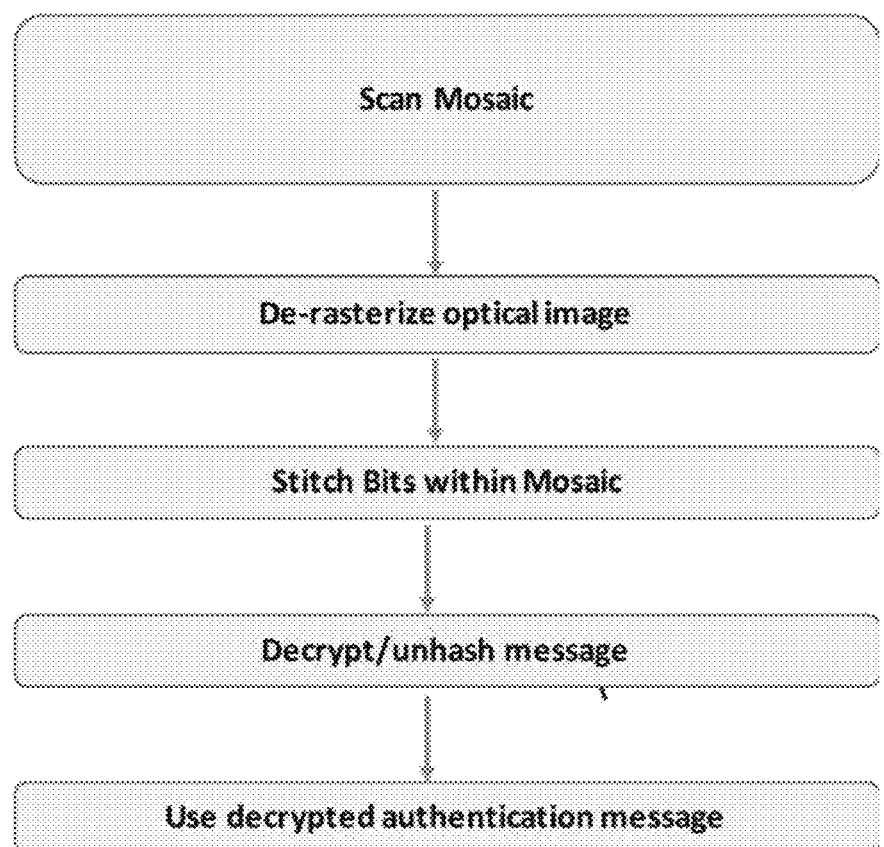
FIGS. 22 and 23 illustrate a multi-party methodology for the present invention.

The present invention is based around optically or wirelessly scannable multiplex codes composed of an enclosed shape defined by a frame which guides the software to the relevant scanning area, as shown in FIGS. 1 and 2. The border is the outermost solid rim of the tag.

As shown in FIG. 3, it is understood that the design of the inventive multiplex code can be various shapes hexagonal, rectangular, triangular, pentagonal, septagonal, octagonal and onwards to an increasing number of sides infinitely and also not limited to polygons (e.g. semicircles, as shown in FIG. 3).

The multiplex code is comprised of a unique pattern of digital tiles (similar to a multiplex code using real tiles) to form a pattern or picture. FIG. 2a demonstrates an example of a digital tile.

The possible composition, arrangement and number of the tiles are infinite. For example in FIG. 2c, the tiles are squares in an outward-winding circular pattern. Alternatively, the tiles may flow outward to the outer rim and turn around to come back in to the center, then return out again till the pattern is complete (see FIG. 4). The tile pattern may include, but is not limited to, the form of shapes such as triangles, circles or squares, stars or hearts.

The tiles in the scanned tag are uniquely arranged by the mobile device or within the server into a hashed/encrypted message. The methodology used for stitching these frames can vary and includes but is not limited to sequential, pattern-based, algorithm-based (example given in FIG. 6). The optical winding of the frames and the stitching together of these frames are two separate decoding steps. Both use similar encoding means shown in FIG. 4.

The extracted message size can be variable—based on encoding parameters. This variable message size may vary the number of tiles. A smaller message is shown in FIG. 1 and a larger message is shown in FIG. 2.

The tiles are shown as squares but they may take the form of any geometry (see FIGS. 3 and 8). The tiles may also be in the form of alpha numerics and symbols such as an exclamation point, heart sign or a smiley face, as shown in FIG. 9. These tiles may also be in the form of a picture or animation. As shown are square frame that are encoded with colored triangles. Any color may be used and instead of triangles, other shapes may be used to generate a frame. A uni-color outline of a frame and the geometry that forms the frame may be used as well.

A color pallet is included in the center of the multiplex code and a series of color pallets are included at the edge of the tag, as shown inFIG. 7. This feature is meant to correct for changes in the environmental color, lighting and shading due to shadows, which may cause a localized discoloration of the multiplex code. The color palettes around the multiplex code and in the center of the multiplex code prevent color variance, shade and glare problems. Each palette of color anchors the colors of the local blocks near it.

This multiplex code may also be without any color, as shown in FIG. 11. This would make it black, white and grey as needed.

Associated software generates unique multiplex codes on a secure server on demand, based on specific requests of authorizer receivers of multiplex codes. Depending on which type of user is requesting the multiplex code, a different type will be made for the specific request. For example, if a 500 pixel width multiplex code is requested by a point of service device to be valid for only 30 seconds, a small multiplex code with the appropriate security messaging will be made to enable that specific multiplex code request. That multiplex code will be invalid after 30 seconds, or some other period of time, of generation and/or receipt.

The multiplex code may be dynamic and rotate and switch frames with a variable time frame. For certain high security applications, new multiplex codes may be requested at specified intervals of time. A new multiplex code will be transmitted by the generator at each interval. The changing nature of rapidly generated multiplex codes means that any hacker would have to start from scratch hacking into each new multiplex code, hence mitigating any chance at hacking to the tag.

The tag can hold forms of identification including a unique ID for the requestor or ID for the request (not only the requestor). The message contained in the tag may hold the time/date it was generated and the interval for which it is valid. The message contained in the tag may hold location information of where the multiplex code is being used in the transaction. The message contained in the multiplex code may hold financial information including but not limited to amount of payment requested by seller. The message contained in the multiplex code may hold seller information including but not limited to name, ID and table location, seating location.

The message contained in the multiplex code may hold part or all of an encryption or hash key. This key may be used in the transaction process to provide further security. The multiplex code may be scanned in part or whole as a rasterized image.

In some embodiments, the multiplex code may be scanned frame by frame instead of a frame map. In other words, the scan recognizes the frame within the multiplex code being scanned and scans it as a character rather than an optical frame map.

In other embodiments, the multiplex code may be scanned in pre-defined component parts, such as some of the frames but not all of them.

For some applications, data on the multiplex code may be replicated in the multiplex code multiple times for reliable usage. Replication of data ensures that challenging lighting and angles of the scan will not corrupt the multiplex code information being scanned. The multiplex code borders and specific orientation points in the multiplex code may be used to recognize and orient the tag by the scanner.

In preferred embodiments, access to the application is only through a secure authentication method such as biometric identification including but not limited to thumbprint, retinal scanner or facial recognition.

In other embodiments, the tag may be an animated projection of a 3D model. Data can be stored more efficiently, more densely and more security as a 3D model. Once the software is activated, it opens straight to either the send fund screen or receive screen. The send fund screen automatically is set to scan for multiplex code—no button is needed to accept a multiplex code. The simplicity of scanning and executing the transaction is novel.

Figure 23:
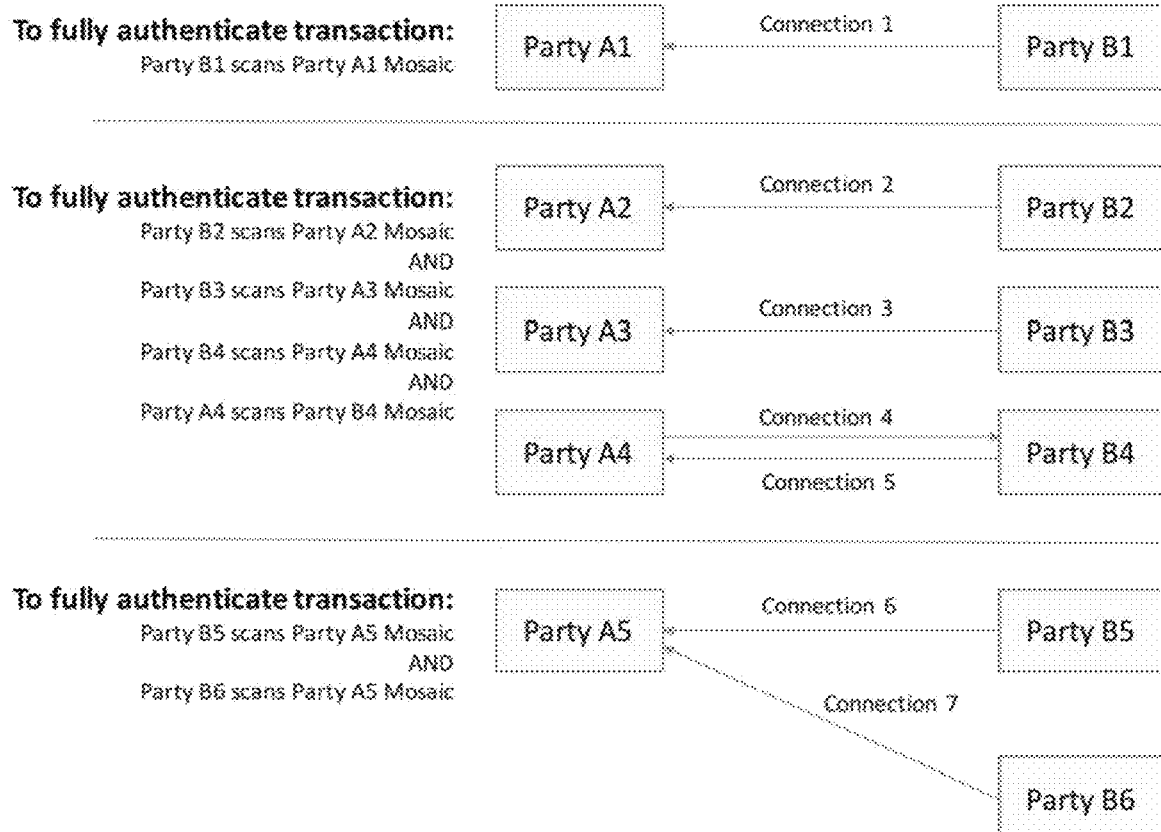

The multiplex code system can be used to authenticate 2 or more parties by scanning one parties multiplex code with another's multiplex scanner. There are two types of scanning for authentication, static and dynamic. Dynamic scan is a real-time multiplex code being scanned (scanning device scans a screen which contains a recently requested multiplex code). Dynamic scan is a real-time multiplex code being scanned (scanning device scans a screen which contains a recently requested multiplex code). Party A requests a multiplex code from a cloud based generator and displays it on their screen. Party B scans the multiplex code in real time. Party B decodes the optical image and optionally decrypts image. This information is transmitted securely to the server, where, if it has not been decrypted on the scanning device, it is decrypted. Party A is validated hereafter or when Party A requests a tag. Party B is validated here. Party C may optionally have scanned party A or another party (D), as shown in FIG. 23. The unencrypted/unhashed multiplex code along with the parties' authentication is used to validate the transaction.

For static scanning, the scanning device scans a pre-printed multiplex code (on a physical object) or permanent/long-term active tag (on screen). Party B is authenticated in the same manner as dynamic scanning. Transaction is validated in the same manner as a dynamic scan. Party A is validated by unencrypting the hash/encryption and displaying identity data for user to validate physically. For example, if someone is selling bananas at a particular address location or perhaps a license #, the multiplex code will be used to derive this information. Party B may be given this information to validate and confirm Party A.

The authority and ability to generate a tag may reside with various unrelated groups for their own purposes such as companies, government agencies or military groups. The tag generating database may be used as a value-added cloud function. The API is a novel way to interface with an optical scan authentication clearinghouse. In certain embodiments, the system may have the ability to aggregate the approval of more than one scan with one more party A and one or more party B because a transaction can take place, as shown in FIG. 23.

The tag client scanning and encryption software may be integrated into other apps. This is a novel way to easily and quickly create security for the targeted app and app environment.

Encryption keys can be broken into multiple portions and saved in different locations to prevent usage of the key in case of unauthorized access to the key database. The multiplex code can also be used as a temporary ID, with it having an expiration period that may or may not be embedded in the multiplex code.

The newly generated multiplex code, with their nearly impossible to duplicate composition as well as the associated expiration times, lead to a secure transfer of information that is not currently available without the hassle of elaborate encoding and decoding systems. Any two parties with the associated software or phone application can easily transfer information back and forth. The sending party generates a temporary multiplex code, the receiving party receives it and authorizes the transfer of whatever information is needed.

The scanning of the multiplex code itself can be done in a number of ways including but not limited to a mobile device scanning a multiplex code from a website, a mobile device scanning a multiplex code from another mobile device, a mobile device scanning a multiplex code from a point of sale device, a mobile device scanning a physical tag to identify the location of mobile holder and/or initiate purchase; a stationary entry point scans a multiplex code from a user's phone or physical ID tag, a mobile entry point scans a multiplex code from a user's phone or physical ID tag, at POS, a user scans multiplex code to conduct a transaction, a multiplex code scanner is used to give entry to electronic systems, for security/military use the system statically and/or dynamically acting as a gatekeeper for entry or gatekeeper for operating machinery, weapons, vehicles, instruments, and appliances.

Respecting the information density required to keep the system secure, it is noted that security comes from a hacker not knowing how the optical encoding works (security through super obscurity). This implicates what the characters are to identify and the order the characters. In addition, security may be obtained through. More particularly, the encryption/cash may be achieved through existing encryption technology.

Generally, amount of data that can be stored in the inventive multiplex code is one-third of the theoretical maximum capacity of the multiplex device. This is the case because substantial capacity is devoted to achieving redundancy. In accordance with the invention, the same message in the inventive multiplex code may be subjected to comparison with the taking of the two that are equal. This is because if the multiplex code is damaged or it is not in a good lighting situation, the inventive multiplex code can still be read.

In accordance with the invention, the inventive system is forgiving of scanning failures amongst the cells and portions of the multiplex code. This is very desirable in order to more reliably read the inventive multiplex code in a wide variety of challenging environmental conditions, such as shadows, low light, glares and lack of focus. In accordance with the invention, the data on the multiplex code may be encoded with the Reed-Solomon Protocol and upon scanning the multiplex code, if there are portions of the multiplex code that are not readable, the inventive system may a protocol such as Golay to enable proper reading of the multiplex code. This combination of protocols one to write and one to read is a significant feature and enables the multiplex code to have a robust ability to be read in most harsh environmental conditions.

The inventive system can store an unlimited size of data. It depends if the size of screen, thus the width of the multiplex code. For example a 500 pixel diameter multiplex code will store about 500 bytes of data.

In respect to the amount of information required to keep the system secured, this depends on the encryption used and is generally understood by those of ordinary skill in the art and not a part of the invention.

The independent dynamic multiplex code cannot be easily aliased because the phone sends a token (an encrypted message) to the multiplex code generator which authenticates the user, then sending a multiplex code to the authenticated requesting party to be scanned by the second party. This token can be generated using the biometric data of the requesting user as one of the variables to encrypt the message so it cannot be aliased.

The inventive printed multiplex code cannot authenticate by itself. The system is designed in this manner because a multiplex code device can be copied. More particularly, the system is safeguarded against such misuse because the printed multiplex code has other data (for example where this multiplex code is located). Optionally this data may be displayed to the user. If it does not visually match, the user is advised to walk away.

In accordance with the invention, users generate tokens which gets validated by the server. Both users must log in using a biometric because only a biometric will allow validation of the user.

In accordance with the invention, the image encryption procedure comprises encoding encrypted information into the image. More critically, the information is compressed (e.g. zipped). The information is repeated, for example, two or more times. Some additional metadata such as the intended length is injected into the encrypted message. The information is encrypted by masking it with a hash-generated string, using the Sovereign algorithm.

The information may then be rendered into an image, for example as above. This may entail, for example by using a violet colored circular outer boundary and center which is drawn to contain the encoding. Color and placement registration marks are added to assist later decryption. The encrypted information is broken up into individual characters. Each character is expressed as a square divided into 4 regions of 8 possible colors each. These squares representing the message data are arranged in a spiral pattern around the center out to the boundary.

In accordance with the image decryption procedure, retrieval of the encrypted information obtaining a photograph of the image. The violet circular boundary, and center are identified within the image. The software determines which way is "up" by utilizing various registration marks. The software assesses the roundness of the image and adjusts for perspective. The software determines the lighting in the image, so that the expected coloring can be anticipated. In accordance with the invention, the software locates and "reads" each of the squares in the spiral around the center.

In accordance with the invention, the message is unencrypted using the Sovereign algorithm in reverse, unmasking the encrypted message with a hash-generated string. The metadata is validated to ensure proper decryption. The message length is derived from the metadata. The two or more repetitive copies of the message are separated back out of the message. The two or more message copies are compared against each other and used for noise and error correction. The best corrected message copy is decompressed (unzipped), resulting in the original decrypted information.

In accordance with the preferred embodiment, the hash-generated strings above used for encryption and decryption are identical. It is noted that identical strings can be generated independently in separate locations by using the same password as the "seed" for the hash.

A particularly preferred embodiment of the present invention will now be described with reference to FIGS. 24-28.

As alluded to above, one of the applications of the inventive multiplex code is in the structuring of and access to a controlled space, and, more particularly by way of particular example, a space where consumer users would be protected from individuals at a higher risk of transmitting infectious pathogens. In accordance with the invention access to such a safe space is limited to people who have been certified in accordance with the requirements for that space.

This object may be advanced by, for example, limiting certification to individuals who have tested positive for an antibody and are therefore unlikely to be transmitters of the pathogen which caused the disease which in turn resulted in production of the antibody by the consumer user's immune system.

By way of another example, certification of the administration of a standard or specialized set of vaccinations may be used to limit access to educational institutions or facilities. Most primary, secondary, and post-secondary schools require students to receive certain vaccinations or receive a certified exemption to attend school. The certification provided by the present invention may be used to grant students access and could also easily be used to certify staff or any contractors, providing a convenient method to protect students which is not otherwise currently feasible.

By way of another example, certification of a prescription for a particular drug or other treatment may be used to authorize the dispensing of drugs to a patient at a pharmacy, medicinal *cannabis* dispensary, or other establishment.

While the above example uses the criteria of, for example, having an antibody or collection of antibodies) indicative of a small probability of transmitting pathogens, for example highly contagious or dangerous pathogens, other criteria may be used, for example social, philosophical or other criteria.

By way of example, certification at a daycare center may be limited to children who have been examined by a psychologist and found to have a predisposition for cooperating and working with peers, nonviolence and inquisitiveness. In this way parents could put their children into an environment where their personal objectives for the development of their children may be met.

By way of another example, certification may be based upon a moral or religious viewpoint, or more generally a philosophical viewpoint whether or not it is associated with an organized religion. In this case, certification would be key to the particular objectives and such certification would be provided by an appropriate professional, for example a clergyman.

Figure 24:
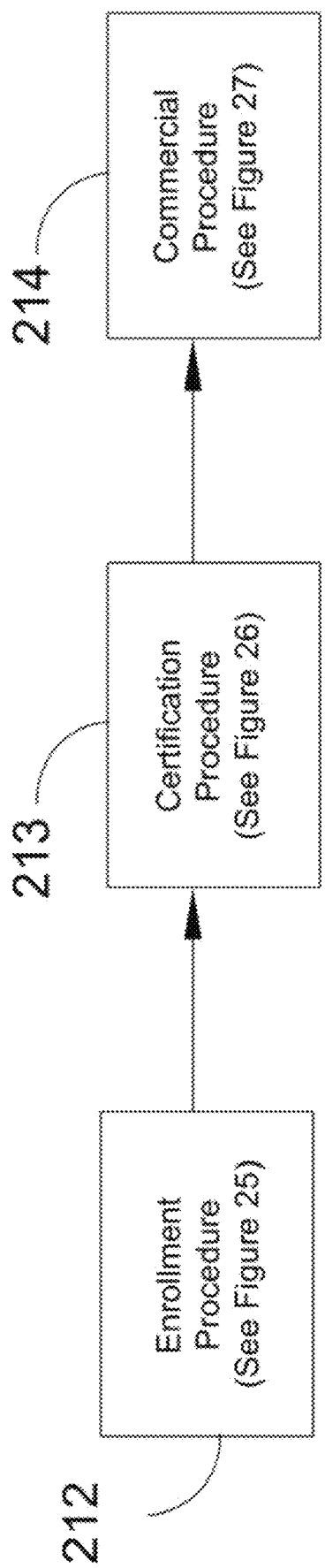
FIG. 24 illustrates the overall inventive method in the context of the creation of safe commercial spaces.

Generally, with reference to FIG. 24, the above objectives are achieved in accordance with inventive method 210. Method 210 comprises, for example, two or more separate portions. More particularly, in accordance with the invention, the inventive method is initiated with an enrollment procedure 310, where consumer users register with the operator of the inventive system. Enrollment procedure 310 is followed by a certification procedure 410. During certification procedure 410, consumer users who have successfully competed enrollment procedure 310 are certified by an appropriate professional, for example, in the case of the promotion of an environment where the transmission of undesired pathogens is low, that professional would be a medical doctor or other health professional trained in the certification procedure, for example, a nurse practitioner.

Following completion of enrollment procedure 310 and certification procedure 410, the inventive system enables an enrolled and certified consumer user to engage in a particular commercial activity by sequencing through the steps in the execution of a commercial procedure 510. This allows the user to gain access to a controlled space, for example a restaurant, a tennis court, a swimming pool, a maker space in a library, a town meeting, an entertainment facility, and so forth.

The invention also contemplates controlling access to mobile venues, for example, a carpooling service or a taxi service such as Uber. It is also noted that, in accordance with the present invention, access to virtual venues may also be controlled.

During enrollment procedure 310 the user registers personal identifying information and biometric data, which is stored in a cloud server for future use. Once enrolled, the user goes through the certification procedure 410, which is executed in conjunction with the entry of certified medical or other information into the user's profile on the cloud server operated by the operator of the inventive process 210.

The next step in the process is the implementation of a particular, for example, commercial transaction or, perhaps more accurately, event or service implemented during the portion of inventive process 210. This portion of the inventive process 210 is designated herein as commercial procedure 510. Completion of commercial procedure 510 results in allowing the user to gain access to, for example, commercial facilities such as restaurants, retail establishments, sporting venues, automobiles, or other physical establishments requiring certification prior to admission, such as medical certification or other certification to gain entry by securely transmitting confirmation of the user's information via the inventive technology.

In accordance with the invention, for example, entry may be physically barred. More particularly, the user may be obligated to present his smart phone to, for example, a person on the other side of the glass door or a car window in order for mechanical lock to allow access.

Figure 25:
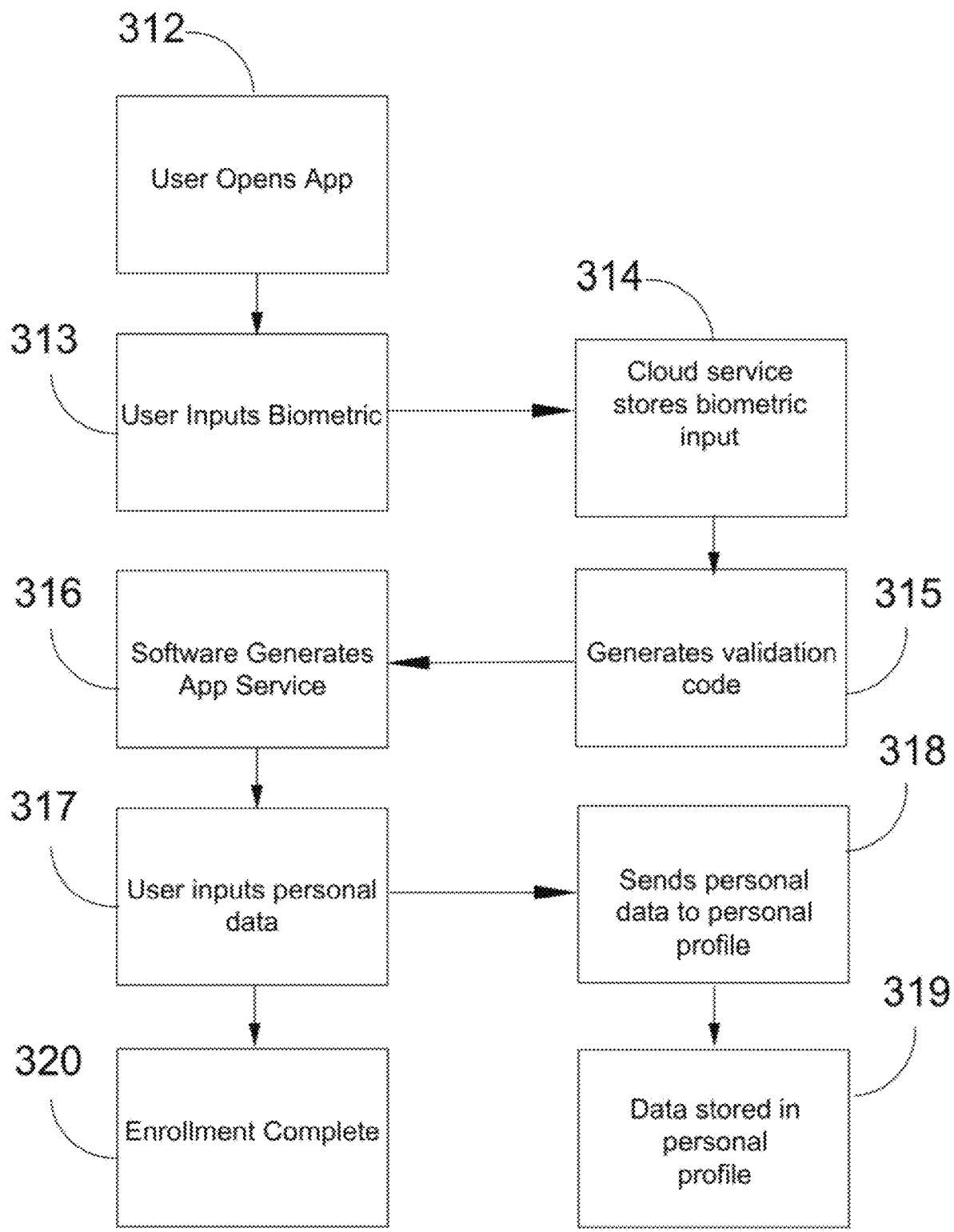
FIGS. 25-27 illustrate details of the method of FIG. 24.

Enrollment procedure 310 of inventive method 210, described in FIG. 25, begins at step 312 where user accesses the inventive software, for example via internet on a smartphone optionally operating Android, iOS, Windows Phone, or other mobile operating system, a personal home computer, or an internet-capable read/display device for multiplex codes. Upon opening the software, prior to full launch of the software, the user enters a biometric such as thumbprint, iris scan, retinal scan, or facial recognition scan, or optionally multiple biometrics 313. The software converts the biometric data into a token or some other form of transmittable data and transmits it to a cloud or other server 314.

Once the biometric token is stored on the server, the server generates a validation code and transmits it to the software 315, which unlocks the remaining software features 316. The user manually enters personal information, including but not limited to name, personal identification numbers, address, phone number, and other identifying information and, optionally, other biometrics not entered in previous steps 317. The software transmits all entered personal information and biometrics to the server 318, which securely stores all data associated with the user in a personal profile 319. Once data are transmitted and stored, enrollment procedure 310 is complete 320.

Figure 26:
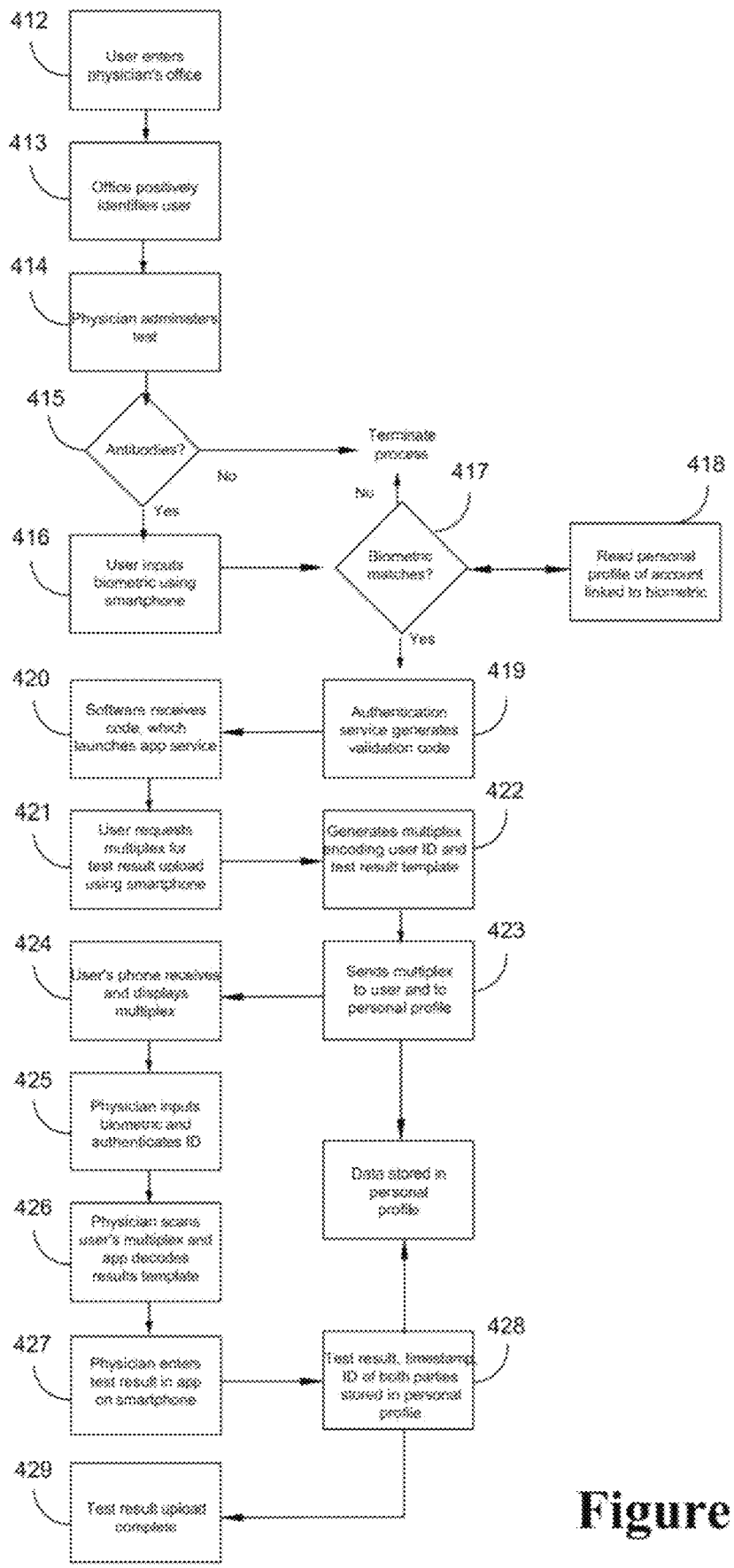

Certification procedure 410 of inventive method 210, described in FIG. 26, begins at step 412 where user presents at a site capable of certifying user's personal information, such as medical information, financial information, personal history, court records, or other sensitive personal information. In an exemplary embodiment, the user presents at a physician's office. The office confirms the user's identity by its typical means of identifying patients 413.

The user then receives a diagnostic medical test or procedure 414, such as that to detect COVID-19 antibodies or other antibody titer, vaccinations, respiratory function tests, or other desired medical examination. If the test returns a negative result, the operation is terminated, but if the result is positive 415 the user inputs a biometric of a type previously stored during enrollment into the user software 416.

The entered biometric is converted into a token, which is checked against the previously stored token by the server's user authentication service 417-418. If the token is not recognized, the operation is terminated. If the token is recognized, the user authentication service generates a validation code and transmits it to the user software 419. Upon receipt of the validation code, the software completes its launch 420.

The user then uses the application to request a multiplex code containing the desired personal information to be encoded along with the desired transaction, in this case a medical diagnostic test 421. The server then generates a multiplex code including personal identity information and a template for medical diagnostic test results and, optionally, an expiration time 422. This multiplex code is temporarily stored in the user's personal profile and is also transmitted to the user software 423.

Upon receipt, the software optically displays the multiplex code 424 or wirelessly transmits an equivalent security device. The physician then inputs a biometric on the physician's smartphone or other reading device 425, triggering the same authorization steps for the physician's identity and launch of the application, as in 416-420 for the user.

The physician then scans the user's multiplex code with a reading device such as a smartphone, multiplex code reader, or other reading device 426, and the multiplex code is decoded by the application software 427. The physician then adds the test results to the template included in the decoded multiplex code, and the test results, authenticated identities of the user and the physician, a timestamp, and the location, and optionally any other information, are transmitted to and stored in the user's personal profile 428. At this point, the certification process is complete 429.

Figure 27:
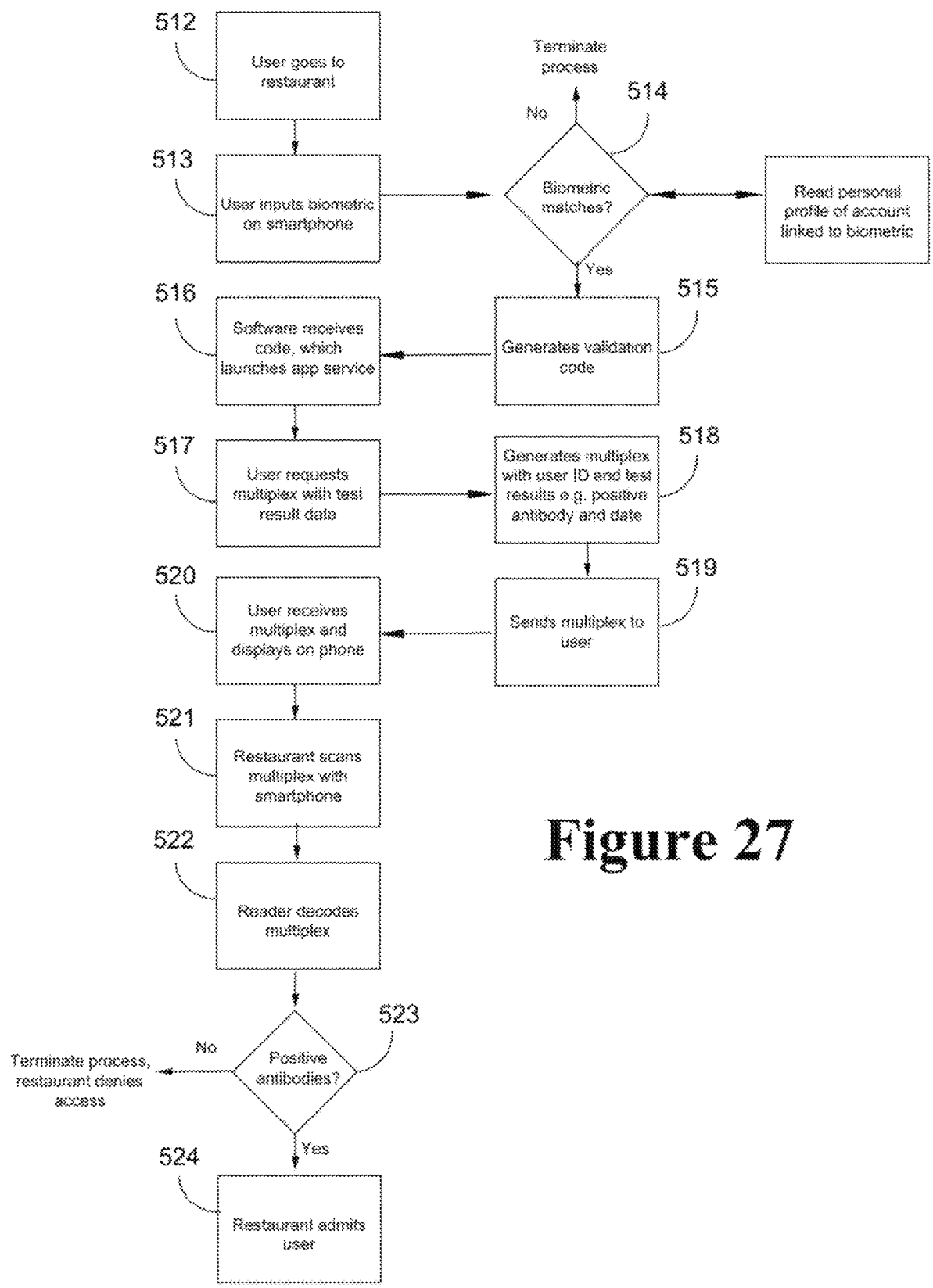

Commercial procedure 510 of inventive method 210, described in FIG. 27, begins at step 512 where the user presents at an establishment requiring certain certified information about the user prior to allowing access, such as a restaurant, retailer, sporting venue, or other physical establishment. In the exemplary embodiment, a user with test results uploaded to the personal profile as described above presents at a restaurant requiring positive COVID-19 antibody test results 512. The user then inputs a biometric of a type previously stored during enrollment into the software 513. The entered biometric is converted into a token, which is checked against the previously stored token by the server user authentication service 514.

If the token is not recognized, the operation is terminated. If the token is recognized, the user authentication service generates a validation code and transmits it to the user software at step 515. Upon receipt of the validation code, the application completes its launch at step 516.

The user then uses the software to request a multiplex code containing the desired personal information to be encoded along with the desired transaction, in this case a verification of positive antibody test results 517. The server then generates a multiplex code including personal identity information and verification of positive antibody test results 518.

This multiplex code is transmitted to the user software 519, and the application optically or wirelessly displays it 520. The restaurant then scans the user's multiplex code with a smartphone, multiplex code reader, or other reading device 521, and the multiplex code is decoded by the software 522. If the decoded message confirms the user's positive antibody test results 523, the user is admitted to the restaurant by an employee, a mechanized locking system connected to the multiplex reader, or some other means 524.

Figure 28:
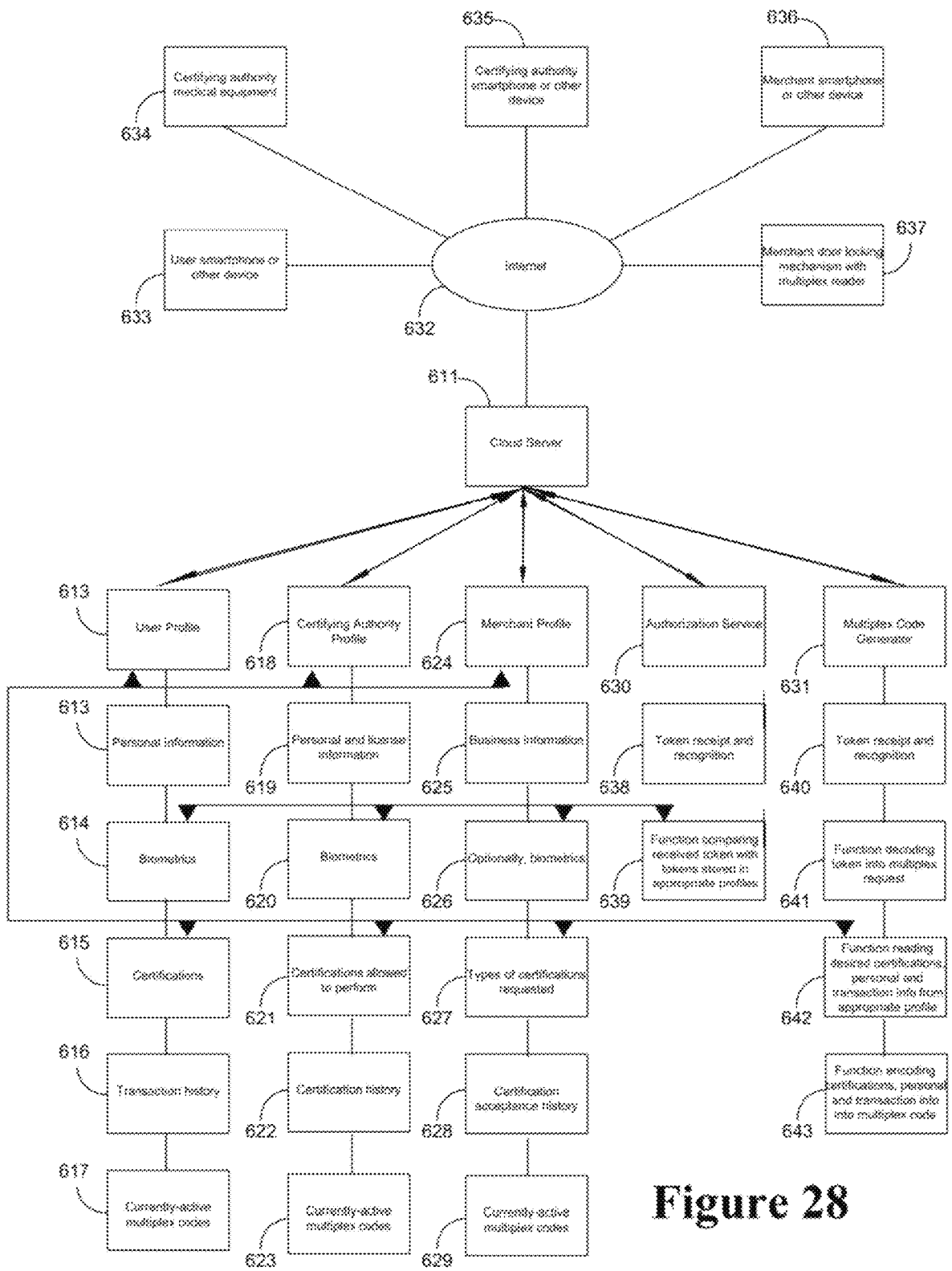
FIG. 28 illustrates hardware for implementing the present invention.

The operation of the system hardware 510 on which the inventive method 210 is implemented, is described with reference to FIG. 28. Cloud server 612 is central to the carrying out of the method steps 310-510, as described above. The server contains non-volatile physical databases, such as hard drives, solid-state memory, solid state drives or the like containing information representing profiles for different types of users, for example consumer users 613, certifying authorities 618 such as physicians, and merchant users 624.

In accordance with the invention, a consumer user profile contains information including personal information 613 such as name, social security number, driver's license number, birthdate, address, phone number, or other identifying information, biometrics scanned during the enrollment procedure 614 (such as a face, fingerprint, and image of the eye, and so forth), any certifications uploaded by certifying authorities such as physicians 615, history of any transactions the user has conducted through the server 616, and any currently-active multiplex codes 617.

In accordance with the invention it is contemplated that the multiplex codes will, optionally, be generated on the fly with respect to a particular authentication transaction and need to be verified by the intended party within a limited period of time.

A certifying authority profile (for example the profile of the doctor who performs test to determine the presence of a particular antibody indicative of, for example, prior infection with a particular pathogen) contains information relating to the certifying authority. Such certifying authorities may be enrolled, much as consumer users are enrolled, and all transactions carried out by the certifying authority (for example doctor or nurse practitioner) would be authenticated using the biometric input by the certifying authority during enrollment. Such information may, and is expected to, include personal information 619 such as name, professional license information, social security number, driver's license number, birthdate, address, phone number, or other identifying information, biometrics scanned during the enrollment procedure 620, listing of any certifications that the certifying authority is authorized to perform 621, such as antibody testing results as in the exemplary embodiment, history of any certifications performed through the server 622, and any currently-active multiplex codes 623.

A merchant profile contains business information 625 such as address, phone number, or other identifying information, a listing of the types of certifications requested of users by the merchant 627, history of any certification accepted 628, any currently-active multiplex codes, and, optionally, employee biometrics for applications requiring identity authentication on the merchant's end 626.

The cloud server containing the user profiles and associated information is connected to the internet 632, which connects the server with users, as described in procedure steps 310-510. The cloud server may be accessed via a consumer user's 633, certifying authority's 635, or merchant's 636 smartphone, tablet, or other multiplex code read/display device. Alternatively, the cloud server may be accessed via any internet-connected equipment at the site of the certifying authority 634, such as medical equipment. The cloud server may also be accessed via a merchant's door locking mechanism connected to the internet and capable of reading multiplex code 637.

The cloud server uses the connection between users and user profiles to run several services, most importantly the authorization service 630 and multiplex code generator 631. The cloud server contains an authorization service capable of token receipt and recognition 638. This function is connected to a further service capable of reading user stored biometric information and comparing it with the newly-arrived token 639.

The multiplex code generator also contains a function capable of token receipt and recognition 640. It also contains a function capable of decoding a token into a multiplex code request 641. A further function reads the requested certifications, personal information, and transaction information and collects the requested information from the appropriate user's profile 642. A further function is capable of encoding the collected information into a multiplex code 643.

In accordance with the invention, the processes detailed above may vary, for example, the buyer could provide the multiplex code, as opposed to the same being provided by the seller. The multiplex code may be generated by the smart phone of the consumer user and not in the cloud.

In addition, various functionalities may be provided in accordance with the invention, such as a "buy now" function. In such a scenario, user may scan a multiplex code to authorize the user to automatically purchase product without requiring the user to enter pricing or any further information.

In accordance with the invention a multiplex code can also be used to act as an authentication and transmission system for block chain data. For example, implementation could involve having a user turn on a block chain app, with a multiplex code transmission option. In this scenario a sending user establishes a multiplex code. A receiving user then scans the multiplex code. The receiver decodes the multiplex code to extract the information for further use.

Examples of information include but are not limited to bank notes, crypo-currency, property lien documentation, etc.

In one case, each user can be considered a blockchain node for a specific transaction and the multiplex code scan acts as an authentication mechanism between the two nodes.

In another case, one user may need to pass block chain information to another user, and use a multiplex code to encode the information.

In another case, an institution, such as a bank, can transmit sensitive blockchain information to users and use a multiplex code to transmit it.

Another possible application is ridesharing or for Haier taxi service (e.g., Uber). In such a scenario, the Uber app indicates that the driver has arrived at the pick up location. Both passenger and driver are logged into the Uber app in accordance with the operation of that application.

When the passenger gets into Uber car, the passenger may, optionally, implement a setting on Uber App on his or her phone to verify the identity of the driver. In principle, this can be done ahead of time.

In this example, the request would go to the Uber cloud. The Uber cloud server determines the identity of the driver and sends the passenger and driver information to access a generated multiplex code in accordance with the present invention. The multiplex code in the inventive server then validates the driver. The multiplex code in the cloud then sends a display multiplex code to the driver's phone. The multiplex code is that displayed on driver's phone the multiplex code is used to validate the passenger in a validation procedure implemented on the server of the website operator utilizing the inventive system to perform authentications.

The passenger that scans driver's phone and the multiplex code is read, followed by a decode and validate operation performed on the server of the operator of the inventive system. This last step may just be used to enable Uber to know that the passenger and driver are now connected together in real life for a specific Uber ride. It also lets the passenger know that this is the right driver and the driver knows this is the right passenger.

Stadium concession usage may also be implemented in accordance with the invention. For example, a sports fan may be sitting in his assigned seat. If the fan wants a concession product such as a pretzel or a soda he simply scans a physically fixed multiplex code associated with his seat, insofar as such a code is adhered to every seat in the stadium.

Alternatively, alternatively a fixed multiplex code may be printed on each ticket, and that code can be scanned by the fan attending the game.

Still yet another possibility is for the user to open a multiplex code App and log in with a bio-metric entry. Upon the occurrence, the identity of the fan may be verified by the server associated with the inventive system. Upon the presentation of a scan window in the inventive application, the user may scan his seat or ticket multiplex code.

The scan multiplex code is sent to the server cloud for verification of the multiplex code by the server operated by the operator of the inventive system. The verified information validates any forward transaction from this seat to the App.

In accordance with the invention of the smart phone of the fan is, optionally, given a set of menu options for concessions and options, for example, for enhanced social media using the app. Likewise, the fan may select items to purchase.

After such selection, the fan may make payment with payment information already provided to the app, without having to reenter the same in much the same manner as cloud services such as Instacart, Amazon, and the like.

In accordance with this embodiment of the invention, the stadium would operate its own server which would receive purchasing information and would be furnished by the stadium system in its standard fashion.

However, while the stadium system, for example operating in the cloud, may use its own payment system to execute the payment, alternatively, the operator of the inventive system may implement payment of the transaction. Once the order is paid for, it is processed and items are delivered to the seat.

As described above, the system may be used for medical testing verification usage, and for other medical purposes. For example user could go to a medical professional for a procedure or for medical testing.

The medical professional then performs the desired medical task. Because the medical professional has already set up a multiplex code account with the operator of the inventive system, the medical professional may input the necessary medical information into his multiplex code app (after bio-metrically logging in)

the consumer user then logs into his or her multiplex code account, for example, bio-metrically and either party can initiate a multiplex code transaction. In such a transaction both the user and medical professional are verified.

For example, the medical professional may be given a multiplex code may be scanned by the consumer user, and this scan then links the test to the multiplex code user and is information record.

Likewise, the medical professional can send test samples to a lab for testing, and when the medical facility receives the test results from the test lab, it can input information to a secure website to be accessed by the user.

Likewise, user may go to a restaurant or some commerce or socializing location that has a safe zone, and the restaurant can scan a user's multiplex code, either manually or automatically.

Alternatively, a person at the restaurant can then visually review medical information on the user's phone. If that individual at the restaurant determines to admit the user into a safe area that filters users based on medical testing and procedure status, the consumer user may enter that area.

Companies and individuals need a technology that enables them to control and/or track the activities of individuals in their organization. This may involve providing access to facilities, providing access to certain records, allowing individuals to input information into databases, allowing individuals to take information from databases, allowing individuals access to communications channels to various persons or classes of persons, and the like. To some extent, such access, permissions and the like may be allocated on the basis of classes of individuals, with certain classes of individuals having the same permissions and the like ("class permissions"). Alternatively, individuals may receive the permissions associated with their class and may also receive additional permissions on an individual basis ("individual permissions"). Similarly, certain permissions may be denied on an individual basis ("individual denials").

Figure 29:
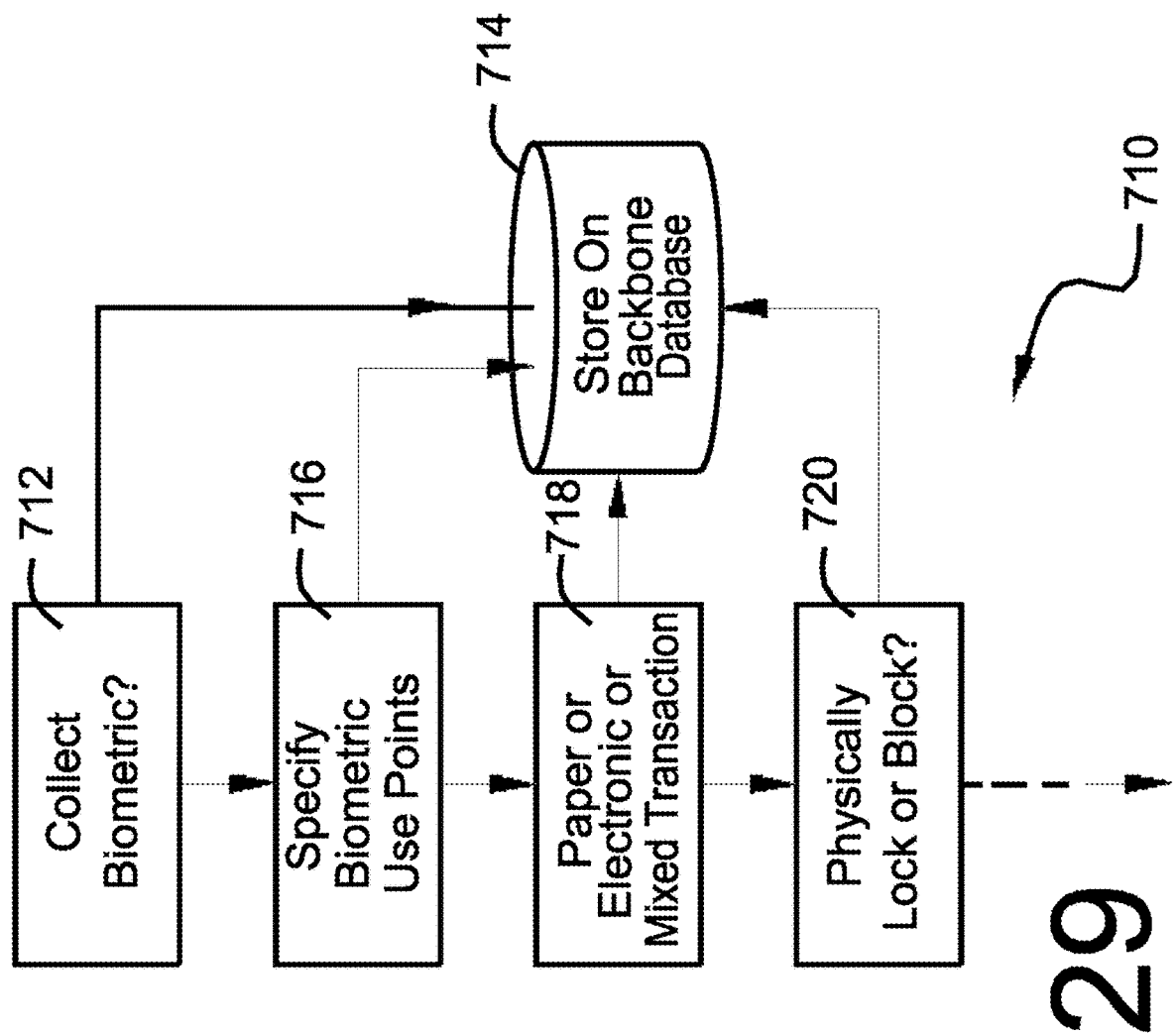
FIG. 29 illustrates the general methodology for a user of the inventive system to customize the inventive method to its particular needs.

FIG. 29 represents the schematic backbone of the system in which a range of selectable software functions and variations of the same may be maintained on the server of the operator of the system for the purpose of providing security to multiple users of the system. More particularly, a system running the inventive process 710 is accessible to users through an interface which may be used by users to customize their own security system in accordance with the embodiment of the invention described above.

Individual and class permissions constitute a layer of security in accordance with the present invention. A second layer of security is keyed to a reliable assignment or authorization protocol. In accordance with the invention it is contemplated that this second layer security is associated with the granting of individual permissions, and, optionally individual denials. The second layer of security may take the form of issuing an individual permission to a person who has been assigned to a particular task. Such issuing of an individual permission would be done by a person in authority either in connection with the giving of an assignment or in response to a request from the individual requesting the individual permission. The granting of the individual permission comprises sending an authorization to, for example, a facility enabling an individual to execute a particular task. For example, the authorization may enable a company email system to allow the person receiving the individual permission to send an email to a specified recipient.

Alternatively, the granting of the individual permission maybe coupled to the sending of a QR code, or the multiplex code of the present invention as described above, to an individual for display on his smartphone to be scanned by a scanner at a particular facility which the individual is being granted access to. That particular facility may be a building, or it may be a piece of equipment, such as a computer which a user wishes to log into, a helicopter, car or the like that would be inoperable, until scanning equipment in the equipment, or located at the building, detects the multiplex code or QR code displayed on the smartphone of the individual seeking entry or attempting to operate the vehicle.

It is noted that while the above example deals with an individual permission, in the case of permissions granted to classes of individuals, similar facilities may be made available without the implementation of an individual permission. Likewise, certain individuals may always have access to certain facilities, and such access is provided in their class definition. Moreover, it is noted that certain permissions may require the approval of multiple individuals, which can be accommodated within the context of the above system.

In accordance with this aspect of the invention, the system at step 710 of the inventive process presents a graphic user interface to the user. In accordance with the invention, the user of the inventive system is contemplated to be any organization, such as a commercial enterprise, a military unit (such as a battalion or pilot in the United States Army), a board of elections, and so forth. The graphic user interface described above allows the organization to determine its own functionality, which forms the backbone of its own specialized and customized security software, and run the functionality on the central server or servers of the operator of the inventive system. For example, the organization may determine whether or not it wishes to use a biometric at step 712. After the selection is made by the user on the graphic user interface provided, for example, over the Internet to the user, the design choice is stored in a database at step 714. If a biometric is selected at step 712, the points in the process where metrics are collected and used may be specified at step 716, and then stored in the backbone database 714.

Other types of functionalities may also be integrated into the customized consumer process backbone. For example, at step 718, the user may specify whether the system being tracked is wholly electronic, paper to the extent that it is possible, or a hybrid approach using both paper and electronic elements. Here again those method processing methodology steps selected by the enterprise are stored at step 714.

In similar fashion, the enterprise may specify whether or not it wishes to introduce a lock or block function, in which the inventive software may perform such tasks as controlling a doorlock, allowing access to communications channels, allowing communications only with specified individuals or classes of individuals for the purpose of minimizing work disruption or similar purpose, allowing access to databases and/or the like.

Figure 30:
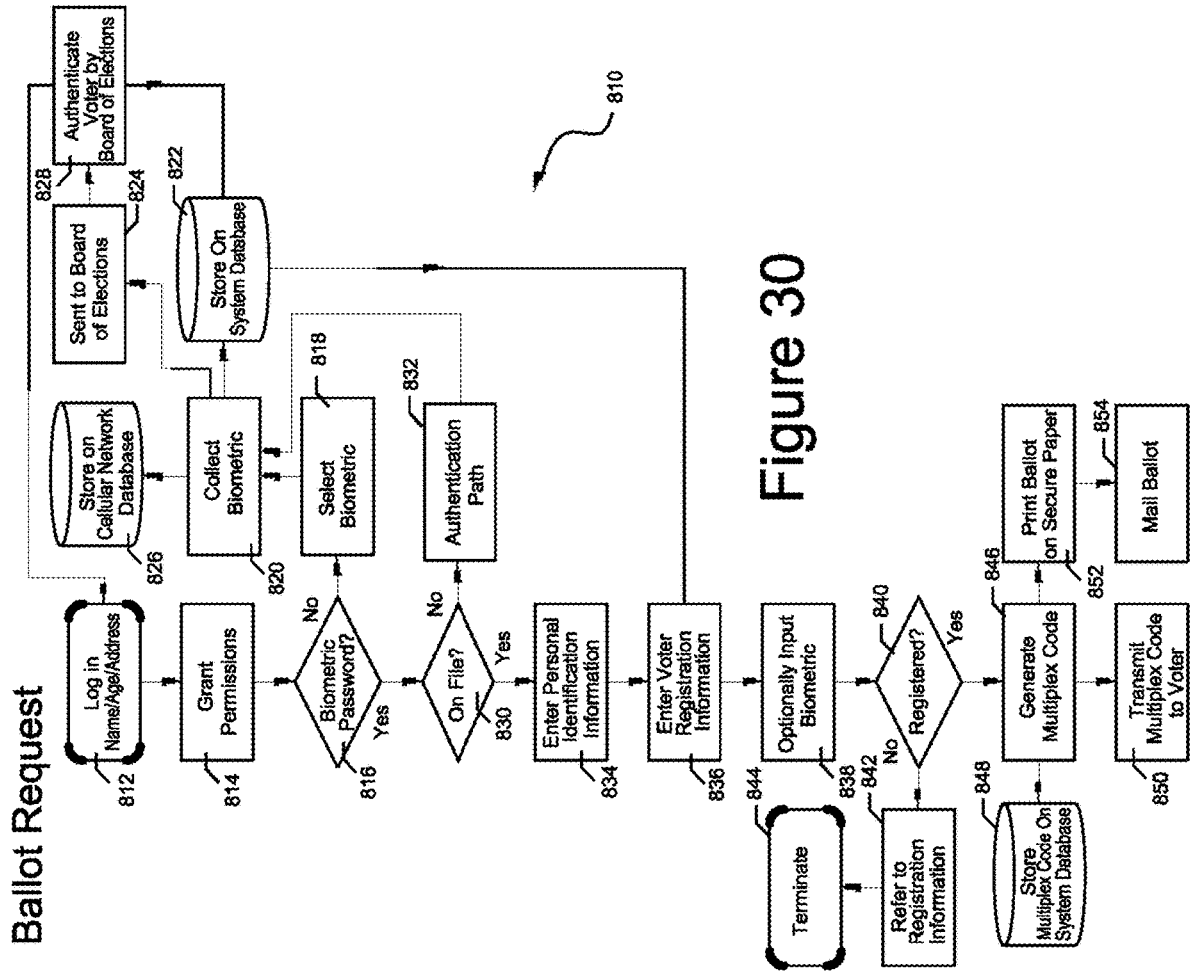
FIG. 30 illustrates the inventive methodology for the generation and transport of an absentee ballot in accordance with the present invention.

Turning to FIG. 30, the operation of the inventive system in connection with a secure "vote by mail" or other absentee ballot method is illustrated. In accordance with this embodiment of the invention, a voter will obtain a paper ballot by using his personal smartphone or other information technology device to employ the inventive system by accessing over the Internet the website of the operator of the inventive system using a dedicated app. The process may be initiated by the system first executing the ballot generation method 810 which is a portion of the overall inventive remote voting method illustrated in FIGS. 30 through 32.

Method 810 begins with a voter who wishes to vote logging into the system at step 812. This may be done by the voter first downloading the app associated with the absentee ballot system of the present invention. In accordance with the invention, a biometric is required in order for the smartphone to be activated. Accordingly, that biometric provide security to the system when the app is downloaded. In accordance with a preferred embodiment of the invention, the app may optionally be associated with a password which the voter sets when he first downloads the app.

Subsequently, upon accessing the system to request a ballot, or accessing the system to execute a ballot by filling out the voter's choice of candidates for various political offices, the voter will put in his password in order to access the system, if this option has been included in the system. Otherwise, reliance may be solely, in this respect on the requirement of inputting a biometric in order to have access to smartphone functionality. This enables generation of a paper ballot to be mailed to the voter, use of the paper ballot including scanning and providing security ensuring passwords and the like, as more fully appears herein.

In accordance with the invention it is contemplated that the voter signs onto the system from his home, or any place where he might be, for example, at work, on business travel at a far destination, or while on vacation away from home. In accordance with the objective of promoting as wide as possible access to the system to existing registered voters without the need for special registration procedures, method 810 may, optionally, be made accessible to all registered voters as recorded in the records of the board of elections of the applicable town, city or other election district. This open access approach is described in connection with FIG. 37, which allows access to all registered voters certified by the board of elections without the need for any additional registration procedure. Alternatively, a special in person voter registration requirement may be implemented in the manner described below.

In accordance with the invention, it is contemplated that such logging in at step 812 is done with the voter's smart phone or other device, for example using the absentee ballot app provided by the board of elections. Upon logging in, the voter is asked to give basic identification information, typically in the voting context being name, date of birth and residence address, and to grant the operator of the inventive system access to information by way of permissions which are granted at step 814. The granting of permission is done in a data input graphic user interface which is presented to the user, for example by means of a graphic user interface of the type which is typically employed in the information technology art.

In accordance with the invention, the system will proceed with the execution of the inventive method 810 if such permissions are granted. Permissions may include access to various items of information and/or system modification on the smartphone of the voter. These may include access to a biometric password, access to personal information, control of hardware on the system such as a camera or fingerprint scanner, and so forth, for example as needed to implement the various functions described in connection with the description of the present invention.

Upon the granting of permissions, method 810 proceeds to a determination, by the software associated with implementation of the inventive method, of whether or not the smart phone of the voter may only be activated through the use of a biometric. This may take the form of, for example, a fingerprint scanner or camera-based face scanner operating in conjunction with prior art or state-of-the-art software for performing these functions. It is noted that this description speaks of the invention in terms of implementation using a smartphone of the voter by way of example. However, it is understood that the present invention may be implemented on other information technology devices, such as tablets, personal computers, iPod™ mini tablets, and so forth, as well as other information technology based devices with a communications capability.

In accordance with the invention, it is contemplated that the operator of the website will be given permission sufficient to enable detection of the means of authentication used by the smartphone or other device to allow the same to be accessed by a user. If it is determined, at step 816 that the device may not be accessed, and thus will remain inoperable, unless it receives a fingerprint, face scanner or, potentially, other reliable input indicating the presence of the owner of the smartphone, the system deems the smartphone secure and proceeds with subsequent steps in the issuing of a ballot to the smart phone user.

However, if a scan of the smartphone of the voter (or more precisely would be voter) indicates that the phone can be accessed by a means which does not require the presence of the voter, the smartphone will be deemed not secure and the process will terminate. However, if the smartphone is secure, for example if it can only be activated by a biometric such as and authenticating fingerprint or facial scan, then the system, on which the inventive method is running, directs the voter at step 818 to the GUI provided on the smartphone for the input of a biometric, as may be available for the particular device. Optionally, this may be done only at the office of the board of elections under procedures which ensure system security and integrity. For example, the methodology steps to be followed for entering a biometric may involve the selection of a particular type of biometric, e.g. a fingerprint scan fingerprint biometric collection or a facial scan of the face of the would be voter. The smartphone then collects the biometric at step 820. Optionally, as alluded to above, the system may require such collection of the biometric to be done at a certifying authority such as the board of elections or other municipal office, and/or before an official, such as the town clerk. The collected biometric is then stored at step 822 in the database of the operator of the system which may be a third party provider furnishing the service to a municipal board of elections, or it may be the board of elections itself.

In accordance with the present invention the collected biometric is viewed as best being authenticated. Accordingly, the collected biometric is sent to the board of elections at step 824. In principle, this could happen in a number of ways. For example, a municipality may require that all uses of the inventive mail-in ballot system appear before the board of elections and program their smart phones to permit only biometric access in the presence of an official of the board and/or in accordance with a particular protocol with the voting app open on the smartphone. This is done by the user logging onto the inventive website of the operator of the electronic mail-in ballot system of the present invention and execute biometric collection at step 820.

Simultaneously with the collection, the biometric is sent to the system database at step 822 as noted above and sent to the board of elections for maintenance on their database at step 824 (in the case where the system is not being operated directly by the board of elections). At the same time, the biometric is stored at step 826 (for example directly on the smartphone itself or on the server of the cell phone service provider) for later use whenever the smartphone is to be activated.

In accordance with the present invention, it is contemplated that authentication may be accomplished by the biometric being taken in the presence of an official of the board of elections, even if the board of elections is not directly operating the system. In this case, the biometric is taken in the app, downloaded by the board of elections onto its computing equipment, and provided by the operator of the inventive software which would provide the biometric to the board of elections at step 824. In accordance with this procedure, upon confirmation of receipt of the biometric by the board of elections, which is indicated by the board of elections using the graphic user interface provided by the operator of the system to the computing equipment of the board of elections, the board of elections also indicates on the graphic user interface that the biometric has been confirmed to be associated with the voter at step 828. The actual authentication entered into the system at step 828 is done in a conventional manner, such as in person presentation of a state issued picture-bearing identification card, passport or the like.

Authentication of the biometric is stored on the database of the operator of the inventive system at step 822 after authentication at step 828. Once the voter has his smartphone set up for biometric activation, and the biometric sent to the board of elections and the website operator, the voter is directed to log into the system at step 812 and cycled through the permissions at step 814 and the check for biometric activation at step 816, as described above.

The system then proceeds to step 830 where the system checks to see if the individual and the individual's biometric is recognized as an identity/biometric which is currently on file with the operator of the system. More particularly, in accordance with the invention, the system, at step 830 verifies that the individual operating the smartphone is known to the board of elections. The biometric ensures that the individual is in the presence of the smartphone. If the person is not known, the system diverts to the generation of a secure biometric. More particularly, if the biometric is not on file, the system proceeds at step 832 along an authentication path to step 820 where a biometric may be collected under reliable authentication circumstances, for example before an official of the board of elections for the town or other municipality involved, as described above. After this the voter is permitted to again, at step 812, logon for the purpose of obtaining a ballot.

If, at step 830 it is determined that the voter and his or her biometric are recognized by the system, the voter is permitted to enter personal identification information at step 834. This information may be cross checked against information maintained by the board of elections as an additional security check. Optionally, the voter is then given the opportunity to enter additional information at step 836, for example, information relevant to the particular election for which a ballot is being sought, or other information being gathered by the board of elections including, information which is not required but which may be voluntarily produced.

The system may then proceed to optional step 840 where it is determined whether or not the registration of the voter is still valid. Such voter registrations may expire after a period of time or when the voter does not vote for a period of years. In the event that the registration of the voter is no longer valid, the system proceeds to step 842 where the voter is informed of steps needed to renew the registration, more particularly to process steps starting at step 820, as described above. The system then proceeds to step 844 where the transaction is terminated.

On the other hand, if the voter's registration is still valid at step 840, the system proceeds at step 846 to generate a multiplex code and store it on the system database at step 848. At the same time, an electronic version of the multiplex code is transmitted at step 850 to the voter where it is stored on the smartphone of the voter. The system then prints a paper ballot at step 852. The paper ballot includes the multiplex code. The paper ballot is then mailed to the voter using the United States Postal Service, a nationally recognized and verifiable service such as Federal Express or DHL, or the like. Alternatively, the ballot may be picked up by a courier, relative, political group dedicated to increasing voter participation or the like, but the same may raise questions with respect to the security of the process.

Alternatively, this may be done completely electronically by the voter accessing the system at the time when he or she wishes to vote. At that time the authenticity of the smartphone and the presence of the voter to operate the smartphone is verified electronically by looking at data on the smartphone and by collection of a fresh biometric.

However, it is believed that paper ballots ensure a measure of accountability, at least in the traditional view, and are more likely to be found to be acceptable by users of absentee ballot procedures. Accordingly, it is anticipated that paper ballots will be printed and mailed as discussed above.

Figure 31:
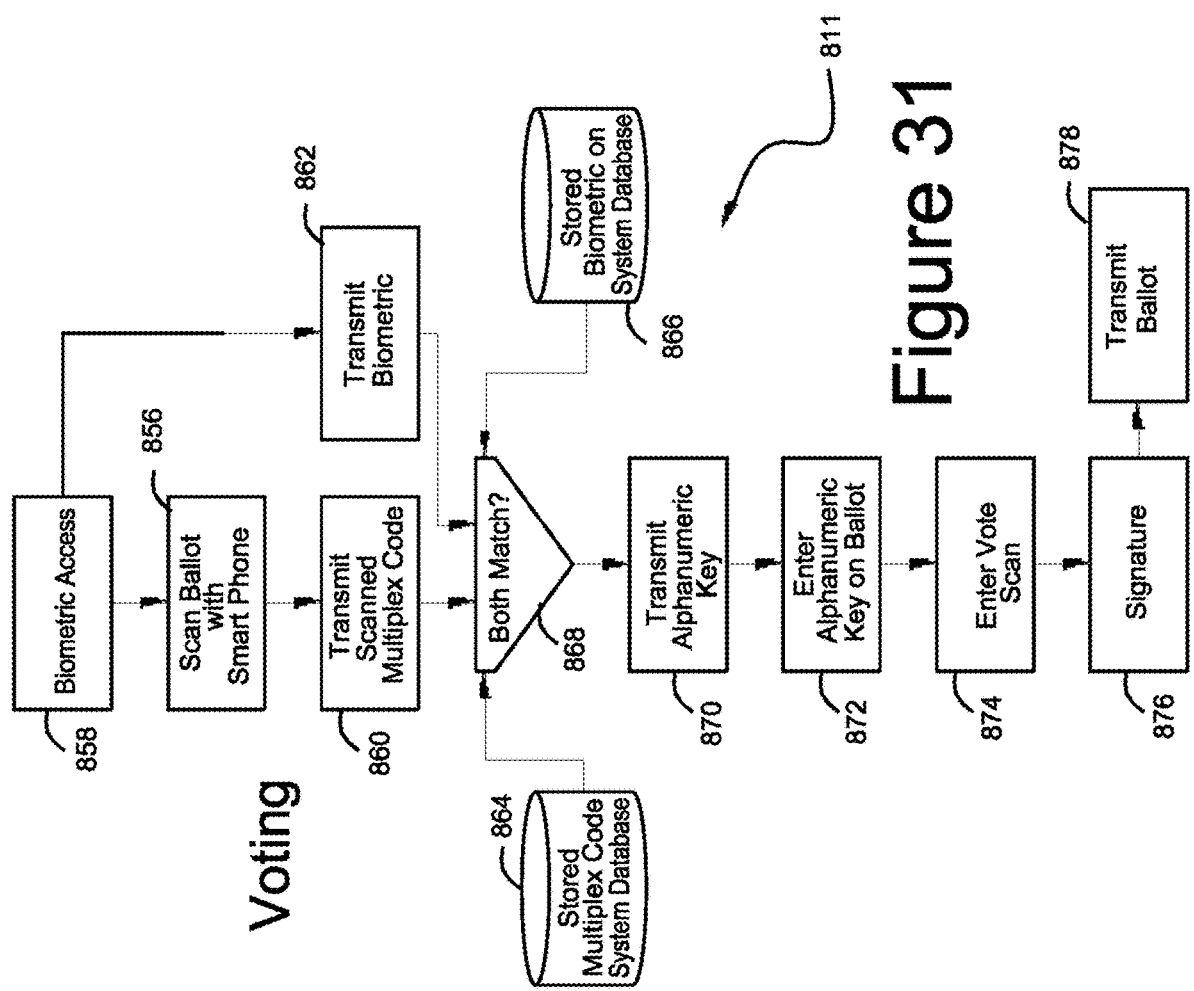
FIG. 31 illustrates the execution of a voting transaction using an absentee ballot in accordance with the invention.

The methodology 811 of the steps in the use of a paper ballot by a voter is illustrated in FIG. 31. After the voter has received the paper ballot, at the time that the voter wishes to vote, the paper ballot is scanned at step 856 by the voter using his or her smartphone after the smartphone has been accessed using a biometric at step 858. This is done by the voter putting in the optional at security password and opening the voting app (or, alternatively, accessing the website of the system operator) on his or her smartphone (or other information technology device or processor) and then using the smartphone camera to scan the multiplex code on the paper ballot and transmit it over the app to the board of elections at step 860.

Similarly, when the voting app is activated using a biometric at step 858, the biometric may be optionally transmitted at step 862, together with identification information for the voter, to the board of elections, as the operator of the inventive system. In accordance with the invention, such identification information includes name, date of birth and current residence address. The inclusion of multiple items of information as identification information and the transmission of information at the time that the biometric and multiplex code are transmitted is intended to increase the security of the system. Optionally, additional security may be provided by requiring the voter to again input the app password or execute another security procedure, for example of the type described herein.

The biometric transmitted at step 862 is then checked at step 866 against the database of biometrics maintained by the board of elections. The biometrics in the board of elections database checked at step 866 were input into that database during the course of the execution of that portion of the inventive method by the inventive system which is illustrated in FIG. 30.

At step 864, the multiplex code transmitted to the board of elections at step 860 is compared to the multiplex codes stored on the database of the system operator (e.g. the board of elections) to see whether it matches the code associated with the voter's name and/or other identification information. Similarly, the multiplex codes in the board of elections database checked at step 864 were input into the database during the course of the execution of that portion of the inventive method by the inventive system which is illustrated in FIG. 30.

If there is a match of both the biometric and the multiplex code with the identification information associated with the voter, the system, at step 868 confirms the same and moves on to step 870 where an alphanumeric key or other authentication information is transmitted to the voter. This serves to provide an added measure of security.

When the voter wishes to vote, he fills out the paper ballot, received for example by way of the U.S. mail, with the voter's selections of preferred candidates presented on the ballot or enters a "write in" choice, which may be exactly in the matter of a conventional paper ballot obtained at a board of elections polling place during in person voting. The voter then, at step 872 fills in the alphanumeric key provided by the board of elections and received by the voter at step 870. The voter may then use his smartphone to scan the multiplex code on the ballot at step 874, after which the ballot is mailed in to or deposited at a board of elections facility at step 878. Optionally, a picture of the filled-in ballot may be taken by the smartphone and transmitted to the board of elections.

In accordance with the invention, it is noted that the steps of the process executed by the inventive system may be executed with equal, lesser or greater effectiveness in a different order which, to the extent not explicitly or impliedly specified herein will be apparent to those of ordinary skill in the art in view of the disclosure in this patent application.

It is noted that in the above described process, the use of the absentee ballot sent by the board of elections to the voter may be done by logging onto an application on the smartphone which communicates information to the board of elections, for example, in real time. Alternatively, the smartphone may be provided with an app which is a simple scanning app for scanning the multiplex code. Because the multiplex code has the capability of carrying a great deal of information, the code can indicate an address on the Internet to which the scanned code is to be sent. For example, under this alternative, the user may simply turn on his cell phone by entering his biometric. Once activated the voter initiates the scanning app, holds the phone over the multiplex code and scans the code. The smartphone then automatically sends the information gathered from the multiplex code by the smartphone of the user to the board of elections. That information includes the identity of the ballot and any other additional information which may be included in order to ensure the authenticity of the scanned code. More particularly, a great deal of information may be included in the code and scanned by the voter, and the volume of information makes it less likely for the multiplex code to the successfully counterfeited. After the scanning has occurred, the board of elections then has information which ensures that it can show that the ballot was in the possession of a registered voter. For example, this information may optionally include information identifying the voter, as well as information giving the date on which the ballot was generated, the election involved, and a testifying number for the ballot itself, and so forth.

In accordance with the invention, it is contemplated that the identification of the voter may optionally be used and then erased from the system to preserve the confidentiality of the vote. Alternatively, that identification information may never be stored by the system, in accordance with an alternative embodiment of the invention described below.

Still yet another alternative is for the election board to print up a great number of generic ballots with unique ballot identification numbers, but without identification information corresponding to a particular voter. When the voter signs onto the system, the inventive system notes that a unique ballot has been sent to a voter and that unique ballot is then sent to the voter. When that voter receives the ballot, he fills it out with his choices for the election and scans the code. The information in the code is sent over the cellular network to the board of elections which can then verify that the unique ballot sent to the voter has been received and executed by a voter because the scanning process is not enabled until the biometric is put into the smartphone to activate the smartphone and allow the scanning app to scan the multiplex code.

In accordance with a further alternative embodiment of the invention, the ballot is created and sent to the voter as described in connection with the description of FIG. 30. However, in accordance with this embodiment, while the ballot is unique, for example by having a number assigned to it, the only record maintained by the board of elections with respect to the ballot with that number is the fact that the number of the ballot is associated with a ballot which has been sent to a voter. No record is made that links the ballot to any particular voter. This preserves the secrecy of the election ballot. When the ballot is mailed to the voter, as described, the system provides a verification that the voter who is intended to get the ballot has been sent a ballot.

At the other end the process, when the voter receives the ballot and scans the multiplex code with his smartphone, the only information transmitted to the board of elections is that the particular absentee ballot with the number stored in its multiplex code has been received by a registered voter, but the system does not know, store or transmit the identity of the voter.

After scanning and filling in the voter's choice, the voter mails in the ballot which is received by the board of elections. The ballot has no identification information associated with the particular voter. Rather, it only has its own unique identification information. In addition, because the scanning app used to scan the multiplex code merely reports that a ballot has been scanned, there is no information of record as to who received the ballot but only that the ballot was scanned by a registered voter.

However, integrity is maintained because records of unique ballots sent out may be checked against records of the scanning of the unique ballots by registered voters. By way of example, if all the unique ballots sent out are returned and no other ballots appear, that proves the integrity of the election. Likewise, if only a portion of the unique ballots are returned, the numbers associated with the returned ballots can be checked against the database of sent out ballots to ensure that only authorized ballots sent to registered voters are being counted in the tallying of the election results. Likewise, if ballots which were not sent out should be mailed to the board of elections, they will not correspond to any sent out ballots and will not be counted.

Figure 32:
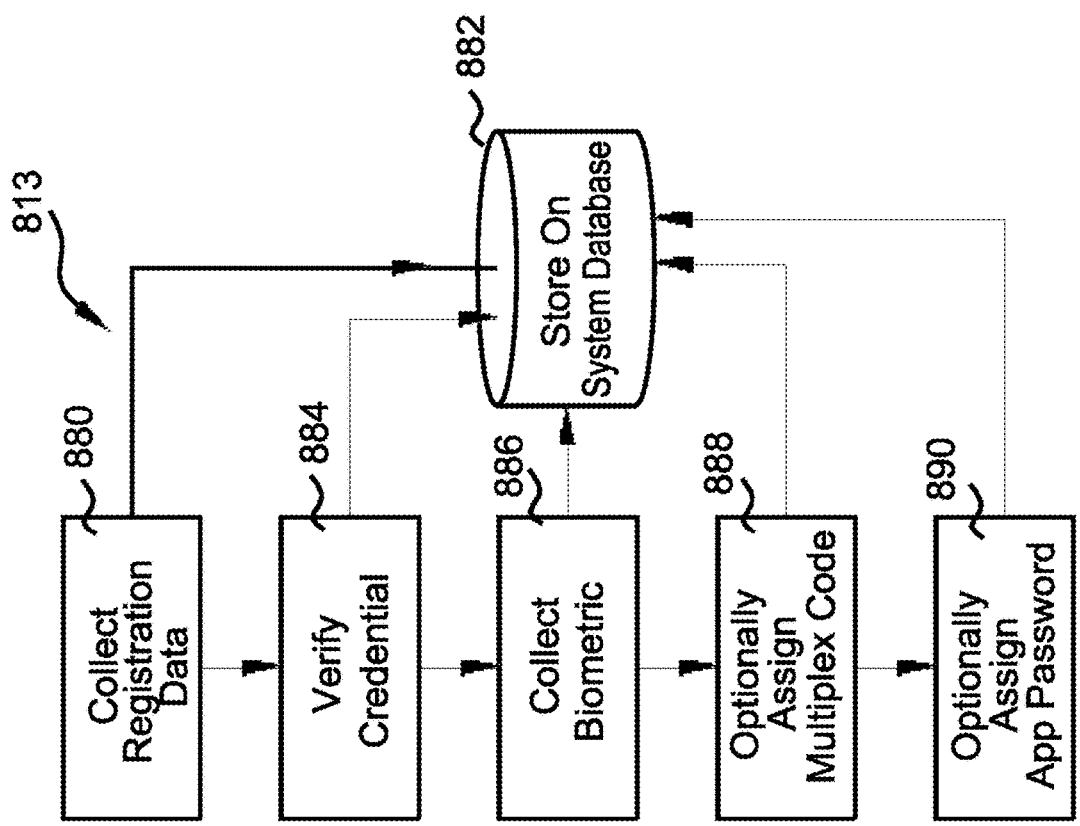
FIG. 32 illustrates the details of an optional voter registration system in accordance with the present invention.

FIG. 32 illustrates an optional registration sequence 813 useful in accordance with the method of the present invention. More particularly, in accordance with sequence 813, registration data is collected at step 880, for example at a board of elections office where the would be voter appears in order to be registered. This may be done by the voter filling out a form at an electronic kiosk located in the office of the board of elections. This data is then stored on the system at step 882. It is noted that the board of elections may elect to have the voter open the absentee voter app provided by the board of elections at the board of elections office, and use his personal smartphone to enter identification data at step 880 in lieu of using a kiosk.

In similar fashion, a board of elections official, before whom the voter is appearing, verifies the identity of the voter through a reliable credential, such as a passport or a state issued identification such as a motor vehicle license, or generic state issued identification. The credential based verification is then input into the system at step 884 by the board of elections official executing such verification on the personal computer of the board of elections official, which personal computer is in communication with the inventive system, for example, by a dedicated absentee ballot application in accordance with the present invention, or an app for accessing and utilizing the inventive system.

Optionally, a biometric may be collected from the voter at step 886 and stored on the system database at step 882. In accordance with the preferred embodiment of the invention, the voter signs on to the inventive system with his smartphone using the downloaded absentee ballot app. With the app open, the biometric is collected by the smart phone and transmitted through the app to the inventive system operated by the board of elections at step 886, where it is stored on the system database at step 882.

Optionally, the system then goes on at step 888 to assign a multiplex code to the voter. This adds another layer of security. In accordance with the present invention, it is contemplated that the multiplex code assigned at step 888 contains predetermined fields for supplementation, for example with the date that the multiplex code is generated. In post voter registration processes of the present invention, such as those described in connection with FIGS. 30 and 31, where a multiplex code is called for, it may, optionally, be the multiplex code assigned at step 888 supplemented with additional information, such as date, to provide additional layers of security. The code generated at step 888 is stored on the system at step 882.

Optionally, if the voter has registered using a kiosk at step 880, the system may assign an app password to the voter at step 890 and store the same at step 882. In accordance with the invention, it is contemplated that when the voter desires to download the app, he must present the app password to the system before being given access to download the app, thus providing an additional layer of security. The assigned app password is stored on the system database of the system of the board of elections at step 882.

Figure 33:
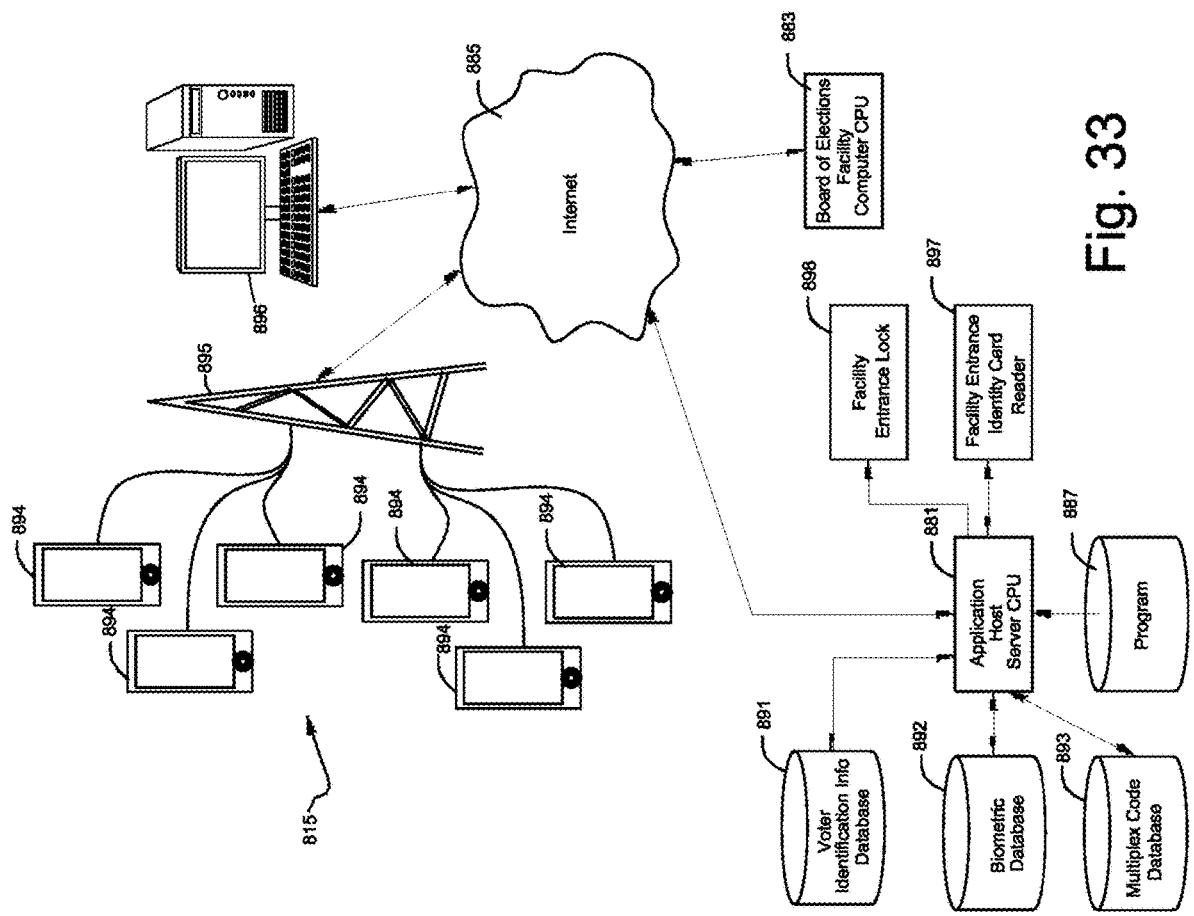
FIG. 33 illustrates the hardware components of the inventive absentee ballot system in accordance with the present invention.

The inventive absentee voter system 815 is illustrated in FIG. 33. System 815 comprises a computer 881 hosting the inventive absentee voter software which is accessed by both the board of elections using the computer 883 of the board of elections official. Computer 883 accesses the application hosted on application host computer 881 by way of the Internet 885 or any other publicly accessible network.

The operation of host computer 881 is controlled by a program 887, which causes the application host computer 881 to execute the steps outlined in FIGS. 29-32 and described in detail in the portions of this patent specification related thereto. Databases maintained by the board of elections are used by host computer 881 to execute such functions. For example, these include, optionally, a multiplex code database 889 which stores multiplex codes associated with the operation of the inventive system 815 as described in connection with the description of FIGS. 29-32. Such databases may include optionally a voter identification information database 891, a biometric database 892 and a multiplex code database 893. In connection with the use of the spiral multiplex codes described herein in the inventive system, it is understood that while the same are given as an example in this description, it is, as an alternative, possible to use a different type of code, or a conventional code such as a QR code, in the system of the present invention.

As described above, the board of elections (and its various offices) may be given access to the inventive system over the Internet which puts them in communication with application host server 881. In addition, voters are put into communication with the inventive system by a dedicated app. Voters use their smartphones 894 to communicate with the inventive system through a wireless provider 895. As an alternative, a smart phone, iPod™, tablet computing device or the like may access the Internet through a Wi-Fi system. Optionally, the system may be accessed through any computing device with a communications capability, such as a personal computer 896.

In accordance with the invention, it is contemplated that the inventive system may optionally control access to a facility or the operation of a mechanical or electronic device, communications channel or the like. Thus, for an added measure of security, a lock to a facility, such as a facility of the board of elections, which may be a drop box for a ballot or an unmanned electronic office, and so forth, may be controlled by the inventive system. For example, the system may cause the unlocking of the facility in response to an identification card at step 897. Alternatively, a facility may be unlocked in response to a user's smartphone 894 being connected by a video communication application to the board of elections, allowing a facial scan and the board of elections then granting access to a facility, for example an unmanned board of elections facility, at step 898.

Figure 34:
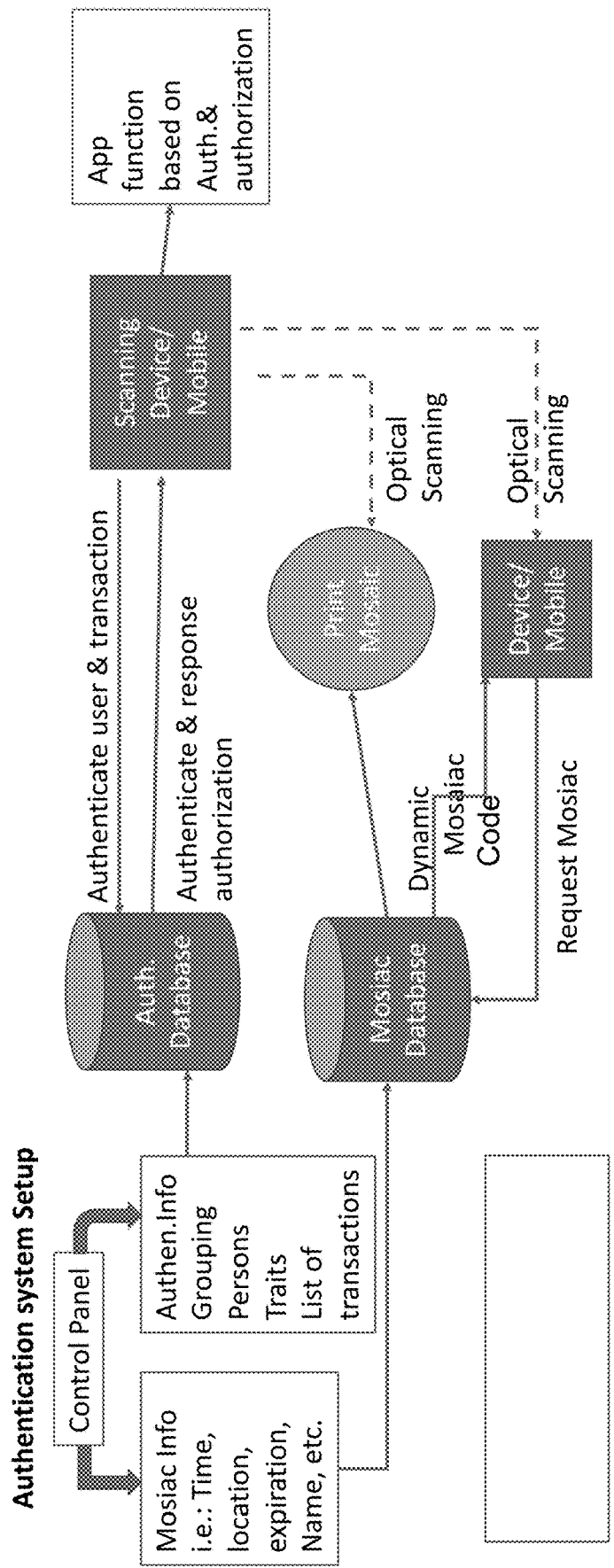
FIGS. 34-36 illustrate optional methodologies for the secure treatment of information in accordance with the invention.
Figure 35:
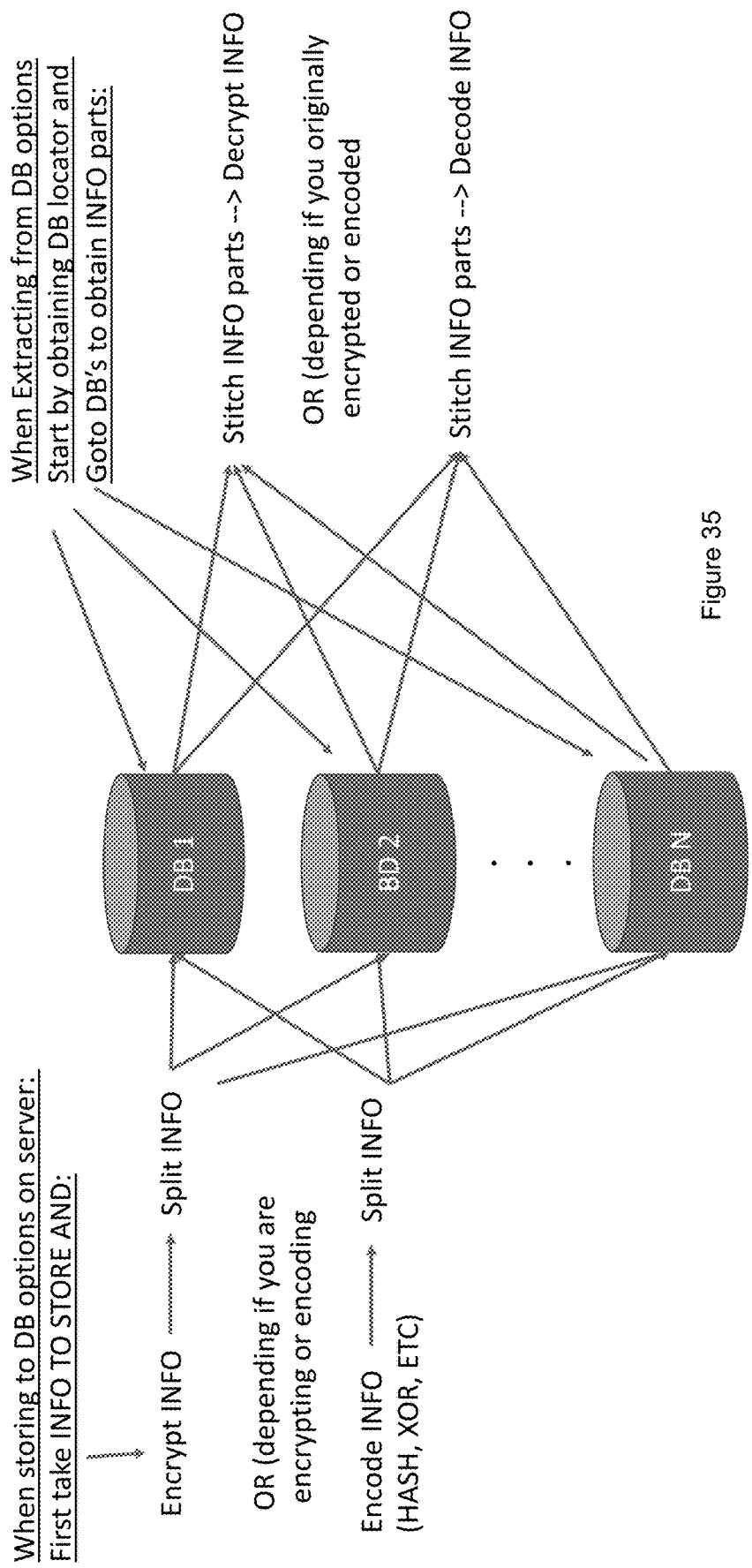
Figure 36:
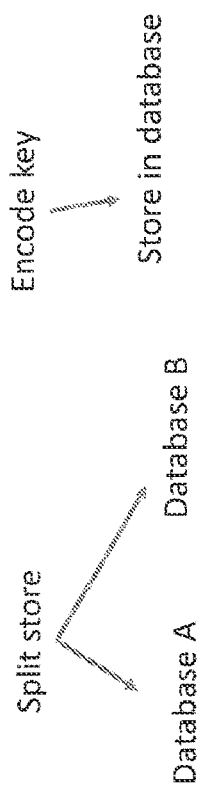

An optional scheme for the treatment of information such as multiplex codes (also referred to herein as "mosaics") is illustrated in FIGS. 34 through 36. Such information may be medical information, identification information for a person or thing, the contents of a ballot, a multiplex or other code, an access key to activate a remote lock or piece of equipment such as a helicopter, and so forth. Referring first to FIG. 34, in the event that the application is to be run on the server of a service provider providing services to multiple organizations or is being provided to a customer to be maintained on the server of the customer, the customer is presented with a graphic user interface comprising a control panel with which to customize the system. This allows the system to be customized. Likewise, software may be provided by download, and the provided software for the app used by the customer to design the functionality to be accessed by way of apps by various users, such as the board of elections, voters, equipment operators, employees, and so forth). In addition to identification information, the inventive system provides various classes with various permissions, as described above. These authorizations are stored in an authorization database as illustrated.

The customers are also provided with a mosaic or other identification code which is stored in a mosaic database. Authorizations are accessed by the system operator in response to presentation of a mosaic, multiplex or other code on the screen of a mobile device such as a smartphone or the like which may be scanned by a facility, for example a facility to which admittance is desired by the consumer owner of the smartphone. Alternatively, other functions may be accessed by a consumer by scanning a printed mosaic or other code, such as a QR code, which appears at a restaurant facility (for example), after which the smartphone transmits the scanned code to the system which checks the authorization database to determine whether a desired action is consistent with permissions associated with the user of the smartphone. In this way, the device or function is turned on based upon the authorization stored on the system.

Likewise, the scanning of another smartphone, for example one owned by or associated with the establishment to which entry is desired, will also serve to transmit, to the processing device running the system software for the operator of the inventive system, the identity of the individual seeking permission, actions, and so forth. In this case both devices may send the multiplex code to the mosaic code database to provide the desired verification. In accordance with the invention it is contemplated that the system may employ dynamic multiplex codes or other dynamic codes which vary, for example including date or other information.

The databases of FIG. 34 may be designed as illustrated in FIG. 35. More particularly, in accordance with the invention it is contemplated that an input information set will be encrypted and then split into, for example, two or more sets of information none of which is complete, but all of which are needed to comprise meaningful information. As an alternative to encryption, information may simply be encoded using a hash function or other prior art encoding technique. At the other end of the information reception/storage/transmission chain, encoded information from different databases is stitched together to reconstitute the original information set.

FIG. 36 illustrates an information encryption and splitting sequence wherein an encryption key is generated by the system prior to the storage of information in the system, and then the encryption key is used to encrypt the information. Optionally, the information may be split into multiple databases, such as Database A and Database B, as illustrated in FIG. 36. Alternatively, for example, simple encoding can be used to store the information in a database.

FIG. 36 generally illustrates the extraction of information which has been encoded or encrypted. In the case where information has been encoded but not split, the recipient of the information is provided with an access key which is used to gain access to the database. In addition, a decoding key is provided to decode the information. Optionally, if the information is encrypted, a decryption key may be used.

Similarly, in the case where information has been split into multiple databases, keys are provided to the information recipient to enable access to the information in the databases, while stitching keys for each of the databases (or optionally a single stitching key) are provided to reassemble the information by stitching the information in the different databases back together again. Optionally, this may be followed by decryption.

In accordance with the invention, it is contemplated that the multiplex codes used by the system will include, optionally a variety of information which relates to the individual. For example, the code, whether it is a multiplex code or other code, can incorporate biometric, location, identification or other information. More particularly, it is contemplated that the information will be broken into units which are embedded into cells. The cells are then integrated into the code. In accordance with the invention, it is contemplated that all codes, for example multiplex codes used by a single user, such as a board of elections, will have the same number of cells, and that the number of cells will be different from the number of cells in the multiplex or other code of another user. This provides an additional layer of security, insofar as to the extent that the code of another user might be a target for wrongdoers, if there is some progress made in hacking another uses code, additional security barriers will exist around the multiplex codes of other users. In this respect, it is believed that the above-described nature of the multiplex code involving a non-rectilinear function provides a measure of security. In addition, it is contemplated that the spiral-like shape will be defined by a plurality of parameters which cause it to divert from a perfect mathematical spiral, for example by varying the length of the graphic units, their thickness, their angle with respect to adjacent units, and so forth according to a function defined by an encryption key, thus providing further layers of security.

It is further contemplated in accordance with the invention that the multiplex code or other code use in accordance with the invention will be able to fully function and provide all information even if graphic units are unreadable, punched out, obscured, subject to glare, lack of illumination, overlapping objects and/or other challenges. More particularly, it is contemplated that failed cells will be ignored and remaining information assembled to result in a fully functional multiplex or other code.

It is thus seen that in accordance with the present invention the technology comprises two parts, namely, an initiator of an authentication process such as a multiplex code or NFC system and a server side authentication system which includes a databased component and software functions that intelligently connect the database to the remote devices such as smartphones. In this way, the system may authenticate and authorize one or more users to perform specified actions. For actions that do not require strong security, these transactions can be initiated by using QR codes or NFC. For secure transactions, authentication and authorization transactions are initiated using NFC with encryption or the spiral multiplex code described herein.

The inventive multiplex codes may be secured through encryption. The multiplex codes can, optionally, hold and transmit private information such as financial information, medical information, location information, and bio-metric information. Necessary private information is first encrypted then, when needed, may be decrypted. The multiplex code can be transmitted via a variety of means such as, but not excluding, optical scanning, email, and web. This private information can selectively be used by the receiving party to conduct an action with the transmitting party including a showing of proof of identity, proof of status, banking information, medical information.

After encryption, information is optionally broken up into multiple blocks of incomplete information to be stored in different places, and, optionally in different geographic locations. This includes personal information which can only be obtained by going to multiple databases, gaining access to the databases decoding the information, and then stitching together information blocks to reconstitute useful information. The result is a multiplex code containing information with a high degree of security. Accordingly, the option exists to provide information in paper form without putting that information on the Internet or databases to be accessed through the Internet, or a hybrid approach where some information is in databases accessed by the Internet and other information can only be accessed through a multiplex code, for example a code printed on a voter's ballot form.

The inventive system also contemplates the incorporation of the scanning device into, for example, a device (such as a car) to which a user wishes access. In this case the user presents his smartphone with a display of a multiplex code on it for the device to scan. If the system verifies the authorization, the automobile is then unlocked.

In accordance with the invention, the authentication system is designed to conform to medical (HIPA) standards financial standards such as DCS PCI and render useless any data that is extracted by breaking encryption through quantum computing or through illicit access to encryption keys. Secure storage of data is critical for adhering to these standards. This invention enables stored data to be further secured by splitting it into two or more separate databases located in different locations, different servers, different database types, different encryption standards. It is noted that the splitting of data can be randomized by first optionally hashing and/or encrypting the data. In cases where the data is split and stored in different locations, quantum computing decryption is rendered ineffective since, in order to obtain any usable aspect of the data, all databases must be accessed and stitched together into a format that can be decrypted and/or unhashed.

The invention contemplates that in order to prevent the theft of encryption/decryption keys, they are optionally split into two or more parts. In order to decrypt the databases, parts of a decryption key will, optionally, need to be stitched together to decrypt and extract the data.

In accordance with the invention, the authentication aspects of the inventive system allow for a multi-partite graph of users that can have a relationship (perform actions) with each other and authenticate and authorize against each other. The universe of this authentication system may host multiple layers of groups that can inherit traits (i.e. authorizations) from each other. These groups can contain more groups. These groups can contain users. Traits can thus provide selective access to various groups/persons without the need for customizing all aspects of an individual's access privileges.

It is also contemplated that the inventive system may operate in accordance with existing artificial intelligence protocols, for example in connection with Internet scrap menus, extract their information and enable, for example, a restaurant to offer a menu-less system with the option of phone based payment systems such as ApplePay and others. This AI system identifies each menu category and translates it into usable items for a phone based menu system with no initial human intervention.

It is contemplated that the present invention may be used in connection with so-called vaccine passports. In accordance with the invention, the process may begin at a medical facility using a strong authentication system such as the inventive spiral multiplex code to authenticate an official or other authorized individual to input medical information such as vaccine information. A patient is given a medical procedure such as a vaccine shot and this information is input into the inventive system by a medical professional. This information, recorded in various locations is provided to businesses and individuals on-demand with the permission of the patient for proof of procedure. At a business location such as a restaurant or sports stadium, the user scans their phone over a multiplex code or NFC or QR code to show proof of medical status.

To ensure the validity of election ballots, a unique ballot for each voter is printed at a local government office. This ballot is sent to the voter with a unique ballot identifier with authentication security such as the inventive multiplex code or a QR code or other code. The user scans/enters the identifier with a bio-metric enabled mobile device. The ballot is filled in and sent back by electronic means or by mail whereupon it is authenticated by another scan process at the government facility.

In this respect the inventive multiplex code may be used to create a safe space and convenience for a user seated at a stadium, for example, the user can scan a localized code or one that is located on a ticket. Once scanned, a user's location is identified by the stadium and the user can order items to his or her seat. The user does not have to pass his or her credit card or money to pay for the concession, it is paid for in the app. The concession arrives and is passed to the requestor at their seat.

Likewise, they financial institution can use the security of the multiplex code combined with the above authentication system to create greater security for their ATM machines, teller windows, safety deposit box (requiring two key scans), and online log ins for the purpose of secure financial transactions.

In addition, if an individual regularly and systematically goes to various location(s) in an office building, and scans a multiplex code to confirm that he has been at each location, the scanning information which occurs multiple times a day may be kept in a database that is accessed by the security, artificial intelligence or other systems.

In accordance with the invention, it is contemplated that security may be provided in numerous situations, such as shared ride services where rider security is a significant issue. When a rider is to enter a car and scans the driver's phone there is a confirmation that both parties are known to the system, this is because the buyer's smartphone and the smartphone of the driver are both only biometrically accessible. This allows all parties involved, the rider, the driver and the ride sharing company to know that the driver is in the presence of the rider. In accordance with the invention, the passenger scanned the driver's unique multiplex code. This allows the system to understand that the passenger is in the presence of the driver. These features are important because a definitive identification of all parties reduces the chances of a rider (or a driver) being exposed to a wrongdoer.

Turning to FIG. 37, an alternative embodiment of the ballot securing system and method 809 of the present invention not requiring in person registration at the board of elections is illustrated. This embodiment makes use of information in the hands of the order of elections and the cellular telephone company. Generally, operation is similar to that of FIG. 30, except as noted.

More particularly, after logging in at step 812 and giving basic identification information including name, date of birth and address, the voter grants information accesss permission to the system at step 814. This enables the system to check a step 817 whether or not the information entered at step 812 matches cellular provider records. In the event that there is no match, the process is terminated at step 819.

If, at step 817 there is a match between information input at step 812 and cellular provider record information, the system proceeds to step 831. At step 831 the system goes on to check to see whether the smartphone is only actually readable upon the entry of a biometric. Alternatively, the system may check to see, more rigorously, whether access to the smartphone has been limited in that fashion since it was purchased, or for a minimum period of months, or other time-based or other standard. If the standard is not met at step 831, for example if the smartphone may be actuated by something other than a biometric, the phone is deemed insecure and the user is sent along and an authentication path at step 832 where the would-be voter selects which type of biometric the voter wishes to use at step 818, generally proceeding to collect a biometric at step 820 which is stored on the cellular network database at step 826 (or, optionally, on the smartphone of the user).

After the biometric is collected at step 820, the app then presents the login screen to the voter at step 812.

Optionally, after the collection of the biometric at step 818 the system may proceed along the steps described in connection with FIG. 30.

Optionally, the same may involve the board of elections to a greater or lesser extent, either in person or virtually, or it may involve trusted agents of the board of elections. Also optionally, the board of elections may choose not to store the biometric of the individual, instead relying upon the cellular network provider to collect and store that information and verify the presence of the voter by providing confirmation, with or without providing the actual biometric, to the board of elections.

If secure biometric access is verified at step 831, the system, at step 840 proceeds to verify that the would be voter is registered and print a secure ballot including a printed multiplex or other code, as described in connection with FIG. 30.

It is noted that the embodiment of FIG. 37 provides a high degree of security, in so far as a ballot is not printed unless the smartphone is in the possession of the owner. Likewise, the ballot is printed with a multiplex code (or other code) and because that multiplex code is unique because of the multiplex code being unique. The unique ballot is then mailed to the voter at his registered address. Likewise, after the ballot has been mailed to the voter, it can be verified that the ballot is in the hands of the voter because the code is unique. More particularly, when the voter votes, he fills in the ballot with his choices for the election. After that, he uses his smartphone camera to scan the multiplex code on the ballot, sending this information to the board of elections and confirming that it is the correct person who has voted. Additionally, an image of the ballot with the multiplex code and the selections of the voter may be transmitted by the app to the board of elections. As noted in connection with description of the embodiment of FIG. 31, additional security may be provided by an optional alphanumeric code.

As noted above, the multiplex code is scanned, for example using the camera of the smartphone, and then the scan is sent to the board of elections over the cellular network. After the board of elections receives the scan of the multiplex code, the board of elections can validate the multiplex code, thus confirming to the board of elections that the voter has seen the ballot. It also tells the board of elections that the ballot received by the voter is the same one which was sent to the voter and intended for his personal use. In addition, positive identification of the paper ballot, once received in the board of elections, can be confirmed by scanning the multiplex code. As noted above, the multiplex code is designed in such a manner that even with losses of numerous graphic units of the code, redundancy in the code ensures that all information in the multiplex code can be retrieved.

This allows the board of elections to count the inventive absentee ballots with a high degree of confidence that the count is correct.

In addition, when the ballot is received in the mail by the board of elections, artificial intelligence may be used to verify the identity of the ballot mailed in with the ballot photographed, optionally by the voter at the time of voting. Likewise, human comparison is possible in the event of any question or issue.

Alternatively, if desired by either the board of elections or the voter, picking up the mail in absentee ballot can be required.

While illustrative embodiments of the invention have been described, it is noted that various modifications will be apparent to those of ordinary skill in the art in view of the above description and drawings. Such modifications are within the scope of the invention which is limited and defined only by the following claims.

What is claimed:

1. A method for printing, sending, receiving and counting absentee ballots, comprising:
   (a) receiving a unique biometric identifier from a would-be voter and inputting the same into a database of registered voters;
   (b) creating a plurality of ballots, each of said ballots bearing a unique code device containing a unique identification code;
   (c) receiving a communication from said would-be voter requesting a ballot, said communication being initiated from a personal computing device;
   (d) verifying that said personal computing device can only be activated by receiving a biometric;
   (e) receiving personal identification information from said would-be voter;
   (f) comparing and associating said received personal identification information with voter record information contained in said database of registered voter information to determine whether said would-be voter is registered to vote;
   (g) in response to a positive identification of said would-be voter as a registered voter, storing in a balloted voter database a notation that said would be voter is to be sent one of said ballots;
   (h) scanning a unique code device on one of said ballots and storing the identification of said ballot in a sent ballots database; and said storing being done with associated identification information associating said ballot with said would be voter,
   (i) sending a ballot whose identification is noted in said sent ballots database to said would-be voter;

(j) receiving a communication from said registered voter using a personal computing device biometric, said communication comprising a locally generated biometric identifier and an output of a scan of the unique code device on said ballot sent to said would-be voter, and said information including the unique identification code;

(k) in response to said communication from said registered voter comprising the output of said scan of said unique code device on said ballot and said locally generated biometric identifier, storing in a voted ballots database the unique identification code of said scanned ballot;

(l) receiving said scanned ballot from said would-be voter annotated with election choices;

(m) repeating steps (b) through (j) for a plurality of voters;

(n) for each of the ballots received from would-be voters, verifying that each ballot is included in the sent-ballots database and is included in the voted ballots database, and verifying that the locally generated biometric identifier associated with the received ballot matches the stored biometric identifier associated with the would-be voter, whereby the ballots that have a matching biometric identifier, and which are included in the sent-ballots database and are identified as verified ballots; and (o) counting the election choices in said verified ballots.

2. A method as in claim 1, wherein said creating a plurality of ballots with each of said ballots bearing a unique code device, comprises creating an optically readable code.

3. A method as in claim 2 wherein verifying that said personal computing device must receive a biometric to become activated comprises noting the identification of the computing device in a ballot computing device database.

4. A method as in claim 1, wherein said creating a plurality of ballots with each of said ballots bearing a unique code device, comprises creating a near field communication device.

5. Apparatus for printing, sending, receiving and counting absentee ballots, comprising:

(a) a printer for creating a plurality of ballots, each of said ballots bearing a unique code device containing a unique identification code;

(b) a would-be voter personal computing device for sending a communication from a would be voter requesting a ballot and for sending personal identification information, wherein said personal computing device can only be activated by receiving a biometric;

(c) a board of elections computing device for receiving a communication from a would-be voter requesting a ballot, said board of elections computing device being coupled to a database of registered voter information including voter biometric identifiers, and said board of elections computing device being operated by software which causes it to execute a program comprising:

(i) verifying that the personal computing device must receive a biometric to become activated;

(ii) receiving personal identification information from said would-be voter personal computing device;

(iii) comparing said received personal identification information with voter record information contained in said database of registered voter information of a board of elections to determine whether said would-be voter is registered to vote;

(d) a balloted voter database for storing a notation of a positive identification of said would-be voter as a registered voter, and for storing in the balloted voter database a notation that said would be voter is to be sent one of said ballots;

(e) a scanning device for scanning said unique code device on one of said ballots;

(f) a sent ballots database for storing the identification of said one ballot in said sent ballots database; and (g) a voted ballots database for receiving an indication that a communication has been received from said registered voter personal computing device of said would be voter, said communication comprising the output of a scan of the unique code device on said ballot sent to said would-be voter, said information including the unique identification code, said communication further comprising a locally generated biometric identifier, whereby returned voted ballots may be assessed for authenticity, wherein said program of steps comprises assessing authenticity of returned ballots by determining that each ballot is included in the sent ballots database and is included in the voted ballots database and have a matching biometric identifier, whereby the ballots that are included in the sent ballots database and in the voted ballots database and have matching biometric identifiers are identified as verified ballots, and the election choices in said verified ballots may be counted.

6. Apparatus as in claim 5, wherein said unique code device comprises an optically readable code.

7. Apparatus as in claim 5, wherein said unique code device comprises a near field communication device.

* * * * *